ilililili US009494568B2

(12) United States Patent
Ng et al.

(10) Patent No.: US 9,494,568 B2
(45) Date of Patent: Nov. 15, 2016

(54) PASSIVE MICROFLUIDIC DEVICE AND A METHOD OF FORMING THE SAME

(75) Inventors: Soon Chye Ng, Singapore (SG); Swee Lian Liow, Singapore (SG); Naiqing Chen, Singapore (SG); Yen Wah Tong, Singapore (SG); Saif Abdul Kadir Khan, Singapore (SG); Boon Sing Fang, Singapore (SG)

(73) Assignee: Neobios PTE LTD, Singapore (SG)

( * ) Notice: Subject to any disclaimer, the term of this patent is extended or adjusted under 35 U.S.C. 154(b) by 312 days.

(21) Appl. No.: 14/376,279

(22) PCT Filed: Feb. 3, 2012

(86) PCT No.: PCT/SG2012/000031
§ 371 (c)(1),
(2), (4) Date: Nov. 12, 2014

(87) PCT Pub. No.: WO2013/115725
PCT Pub. Date: Aug. 8, 2013

(65) Prior Publication Data
US 2015/0072374 A1 Mar. 12, 2015

(51) Int. Cl.
*G01N 33/00* (2006.01)
*C12N 5/076* (2010.01)
*G01N 33/483* (2006.01)
*C12M 1/00* (2006.01)
*B01L 3/00* (2006.01)
(Continued)

(52) U.S. Cl.
CPC ......... *G01N 33/4833* (2013.01); *B01L 3/5027* (2013.01); *C12M 47/04* (2013.01);
(Continued)

(58) Field of Classification Search
CPC .............. C12N 5/061; C12N 5/0612; B01L 3/520753; B01L 3/50273; B01L 3/502761; B01L 2300/087; G01N 15/147; G01N 2015/149; G01N 33/4833; G01N 33/487; G01N 33/5029; C12M 23/16
See application file for complete search history.

(56) References Cited

U.S. PATENT DOCUMENTS

2006/0270021 A1* 11/2006 Takayama ........... B01L 3/50273
435/283.1
2010/0291535 A1* 11/2010 Yao ...................... C12N 5/0612
435/2
2011/0061472 A1 3/2011 Wo et al.

FOREIGN PATENT DOCUMENTS

GB 2430393 A 3/2007

OTHER PUBLICATIONS

Brenda S. Cho et al., "Passively driven integrated microfluidic system for separation of motile sperm," Analytical Chemistry, 2003, vol. 75, pp. 1671-1675.
(Continued)

*Primary Examiner* — Jennifer Wecker
(74) *Attorney, Agent, or Firm* — Calfee, Halter & Griswold, LLP

(57) ABSTRACT

According to embodiments of the present invention, a passive counter flow free microfluidic device for sorting a sample of flagellated cells is provided. The passive counter flow free microfluidic device includes an input reservoir configured to receive the sample of flagellated cells, an output reservoir positioned downstream of the input reservoir, the output reservoir configured to collect the flagellated cells that are sorted, and a plurality of microchannel sections arranged sequentially and in fluid communication with each other between the input reservoir and the output reservoir, and designed to define a closed microchannel system between the input reservoir and the output reservoir, wherein each microchannel section comprises at least one microchannel, wherein an inlet of the microchannel of a first microchannel section of the plurality of microchannel sections is connected to the input reservoir, wherein an outlet of the microchannel of a last microchannel section of the plurality of microchannel sections is connected to the output reservoir, and wherein, for each microchannel section, the total volume of the microchannels of one microchannel section of the plurality of microchannel sections is larger than that of the respective in said downstream direction subsequent microchannel section of the plurality of microchannel sections for sorting the flagellated cells when the flagellated cells move from the input reservoir to the output reservoir.

20 Claims, 13 Drawing Sheets

(51) Int. Cl.
G01N 33/487 (2006.01)
G01N 15/14 (2006.01)
C12M 3/06 (2006.01)
C12N 5/071 (2010.01)
A61D 19/00 (2006.01)

(52) U.S. Cl.
CPC ........... A61D 19/00 (2013.01); B01L 3/50273 (2013.01); B01L 3/502753 (2013.01); B01L 3/502761 (2013.01); B01L 2200/0652 (2013.01); B01L 2300/087 (2013.01); B01L 2300/0816 (2013.01); B01L 2300/0861 (2013.01); C12M 23/16 (2013.01); C12N 5/061 (2013.01); C12N 5/0612 (2013.01); G01N 15/147 (2013.01); G01N 33/487 (2013.01); G01N 2015/149 (2013.01); Y10T 29/49826 (2015.01)

(56) References Cited

OTHER PUBLICATIONS

R. John Aitken et al., "Significance of reactive oxygen species and antioxidants in defining the efficacy of sperm preparation techniques," J Androl, 1988, vol. 9, No. 6, pp. 367-376.

Armand Zini et al., "Influence of semen processing technique on human sperm DNA integrity," Urology, 2000, vol. 56 (6), pp. 1081-1084.

Jason M. Wu et al., "A surface-modified sperm sorting device with long term stability," Biomed Microdevices, 2006, vol. 8 (2), pp. 99-107.

Koji Matsuura et al., "Screening of sperm velocity by fluid mechanical characteristics of a cyclo-olefin polymer microfluidic sperm-sorting device," Reproductive BioMedicine Online, 2011.

T. Qiu et al., "A microfluidic 'treadmill' for sperm selective trapping according to motility classification," Transducers'11, Beijing, China, Jun. 5-9, 2011, pp. 1320-1323.

Duckbong Seo et al., "Development of sorting, aligning, and orienting motile sperm using microfluidic device operated by hydrostatic pressure," Microfluid Nanofluid, 2007, pp. 561-570.

Duckbong Seo, "A development of the motile sperm sorting microfluidic devices," Dissertation presented to the Faculty of the Graduate School University of Missouri-Columbia, 2007.

Sherrie G. Clark et al., "Reduction of polyspermic penetration using biomimetic microfluidic technology during in vitro fertilization," Lab on a Chip, 2005, vol. 5, pp. 1229-1232.

* cited by examiner

PASSIVE MICROFLUIDIC DEVICE AND A METHOD OF FORMING THE SAME

CROSS-REFERENCE TO RELATED APPLICATION

This application is the U.S. national phase entry of PCT/SG2012/000031, with an international filing date of 3 Feb. 2012, the entire disclosure of which is fully incorporated herein by reference.

TECHNICAL FIELD

Various embodiments relate to a passive counter flow free microfluidic device and a method of forming a passive counter flow free microfluidic device, in particular relating to a passive counter flow free microfluidic device for sorting a sample of flagellated cells. Various embodiments further relate to a method for sorting a sample of flagellated cells using the passive counter flow free microfluidic device and use of the passive counter flow free microfluidic device for sorting spermatozoa.

BACKGROUND

Conventional in vitro fertilization (IVF) techniques of sperm sorting consist of either (1) a direct swim-up method or (2) density gradient separation. For the direct swim-up method, sperm DNA integrity may be compromised and low yield of recovered motile spermatozoa was observed in some studies [A. Zini, et al., "Influence of semen processing technique on human sperm DNA integrity", Urology, 56 (2000) 1081-1084]. For the density gradient separation technique, repetitive centrifugation and re-suspension of the seminal pellet may cause damage to motile spermatozoa by reactive oxygen species [R. J. Aitken, J. S. Clarkson, "Significance of reactive oxygen species and antioxidants in defining the efficacy of sperm preparation techniques", J. of Androl., 9 (1988) 367-376].

Microfluidic technology has shown great promise as a revolutionary platform for in vitro fertilization (IVF). Depending on the design of microfluidic devices, there are many possibilities for which the microfluidic devices could simplify or improve the current IVF procedures.

SUMMARY

According to an embodiment, a passive counter flow free microfluidic device for sorting a sample of flagellated cells is provided. The passive counter flow free microfluidic device may include an input reservoir configured to receive the sample of flagellated cells, an output reservoir positioned downstream of the input reservoir, the output reservoir configured to collect the flagellated cells that are sorted, and a plurality of microchannel sections arranged sequentially and in fluid communication with each other between the input reservoir and the output reservoir, and designed to define a closed microchannel system between the input reservoir and the output reservoir, wherein each microchannel section comprises at least one microchannel, wherein an inlet of the microchannel of a first microchannel section of the plurality of microchannel sections is connected to the input reservoir, wherein an outlet of the microchannel of a last microchannel section of the plurality of microchannel sections is connected to the output reservoir, and wherein, for each microchannel section, the total volume of the microchannels of one microchannel section of the plurality of microchannel sections is larger than that of the respective in said downstream direction subsequent microchannel section of the plurality of microchannel sections for sorting the flagellated cells when the flagellated cells move from the input reservoir to the output reservoir.

According to an embodiment, a method of forming a passive counter flow free microfluidic device for sorting a sample of flagellated cells is provided. The method may include forming an input reservoir configured to receive the sample of flagellated cells, forming an output reservoir positioned downstream of the input reservoir, the output reservoir configured to collect the flagellated cells that are sorted, and forming a plurality of microchannel sections arranged sequentially and in fluid communication with each other between the input reservoir and the output reservoir, and designed to define a closed microchannel system between the input reservoir and the output reservoir, wherein each microchannel section comprises at least one microchannel, wherein an inlet of the microchannel of a first microchannel section of the plurality of microchannel sections is connected to the input reservoir, wherein an outlet of the microchannel of a last microchannel section of the plurality of microchannel sections is connected to the output reservoir, and wherein, for each microchannel section, the total volume of the microchannels of one microchannel section of the plurality of microchannel sections is larger than that of the respective in said downstream direction subsequent microchannel section of the plurality of microchannel sections for sorting the flagellated cells when the flagellated cells move from the input reservoir to the output reservoir.

According to an embodiment, a method for sorting a sample of flagellated cells is provided. The method may include supplying the sample of flagellated cells to the input reservoir of the passive counter flow free microfluidic device as described herein.

According to an embodiment, there is provided use of the passive counter flow free microfluidic device as described herein, for sorting spermatozoa.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIGS. 5A to 5D show schematic top views while

FIGS. 5F to 5H show schematic top views while

FIGS. 6A to 6D show schematic top views while

FIGS. 6F to 6I show schematic top views while

DETAILED DESCRIPTION

Figure 1:
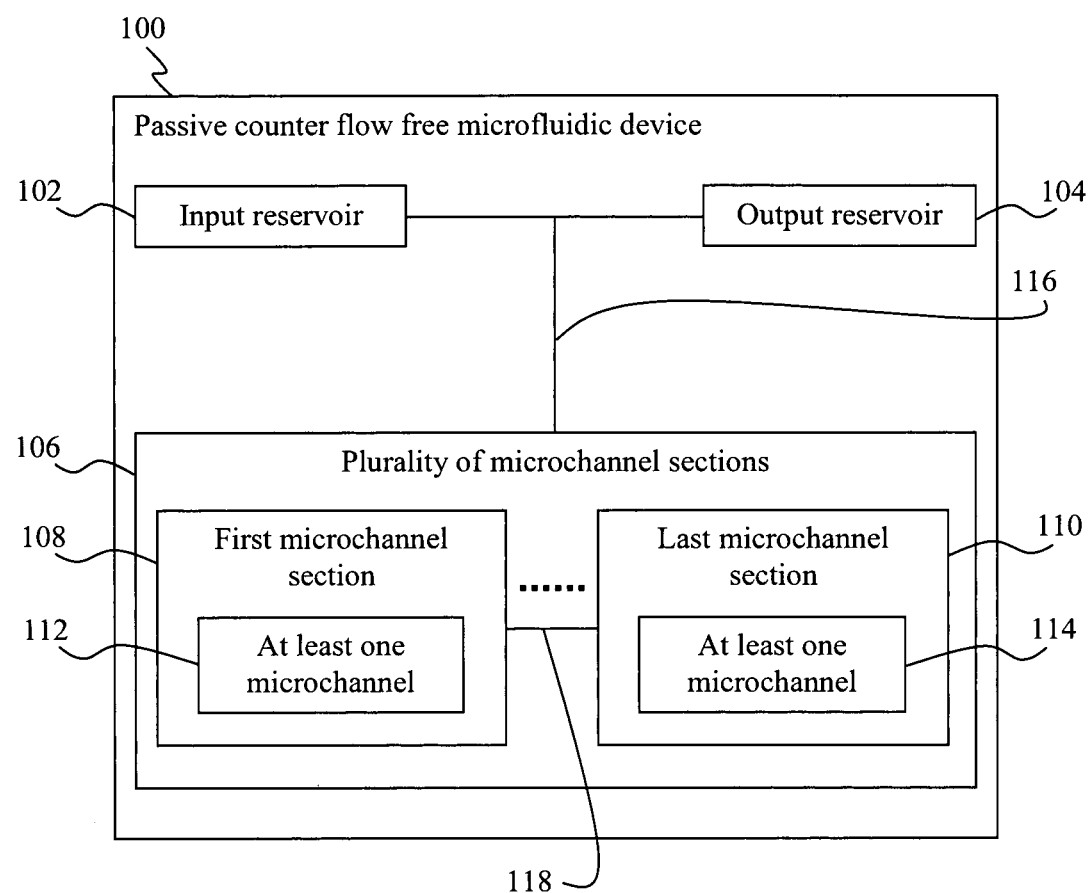
FIG. 1 shows a schematic block diagram of a passive counter flow free microfluidic device for sorting a sample of flagellated cells, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural and logical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other method or device. Similarly, embodiments described in the context of a method are analogously valid for a device, and vice versa.

In the context of various embodiments, the phrase "at least substantially" may include "exactly" and a variance of ±5% thereof. As an example and not limitations, "A is at least substantially same as B" may encompass embodiments where A is exactly the same as B, or where A may be within a variance of ±5%, for example of a value, of B, or vice versa.

In the context of various embodiments, the term "about" or "approximately" as applied to a value may encompass the exact value and a variance of ±5% of the value.

As used herein, the term "and/or" includes any and all combinations of one or more of the associated listed items.

Various embodiments may provide a passive counter flow free microfluidic device or a microchannel device for sorting flagellated cells, for example including any self-propelled (flagellated) cells (e.g. single-celled organisms) and/or motile cells (e.g. single-celled organisms). The passive counter flow free microfluidic device performs sorting based on progressive volumetric confinement, where highly motile sperm may move in or across confined space or volume, whereas less or non-motile sperm may encounter difficulties to move in or across such confined space or volume.

As examples and not limitations, the passive counter flow free microfluidic device of various embodiments may have a sample reservoir (e.g. an input reservoir or input well) containing untreated semen or where untreated semen may be loaded, a collection reservoir (e.g. an output reservoir or output well) for collecting or harvesting motile sperm (or sperm that are sorted), and a fluid-filled microchannel-based 'obstacle course' configured to physically select the fittest sperm as the sperm move from the input reservoir to the output reservoir on the passive microfluidic device. The physical principle of this 'obstacle course' is hydrodynamic confinement or volumetric confinement—a sperm experiences greater resistance to its inherent, active swimming motion when placed in a confined environment, compared to in an unconfined environment. This may allow only the highly motile sperm to swim or move into and through the confined environment. In various embodiments, at least one cross sectional dimension (e.g. width and/or depth) of one or more microchannels of the passive microfluidic device of various embodiments may be comparable to the cross-sectional size of a single sperm, which may be a few micrometers in size (e.g. about 2 μm), to provide a confined environment. However, it should be appreciated that the microchannel(s) may have a width and/or depth larger than the cross-sectional size of a single sperm, for example a width and/or depth between about 2 μm and about 20 μm.

In the context of various embodiments, the term "comparable" as applied to a size or dimension may include a variance of +30% of that size or dimension.

In various embodiments, the 'obstacle course' may be a network of microchannels or microfluidic channels between the input and output reservoirs, with a progressive increase in confinement in going from the input reservoir to the output reservoir. The structured, directional gradient in the degree of confinement from the input reservoir to the output reservoir may be designed and optimized to ensure that only the fittest sperm complete the journey across the microfluidic device or chip, from the input reservoir to the output reservoir via the network of microchannels. These spermatozoa may then be harvested by aspiration from the outlet reservoir and used for subsequent processing, for example off-chip fertilization, or direct in vitro fertilization (IVF) if oocytes are placed in the outlet reservoir.

In various embodiments, the structured 'confinement gradients' may include 2-D confinement, for example due to narrow and long microchannels or microchannel 'tubes'. As an example and not limitations, the input reservoir and the output reservoir may be joined, coupled and/or in fluid communication with a plurality of microchannel sections or arrays, e.g. the input reservoir and the output reservoir may be coupled and/or in fluid communication with serial or sequential sections or arrays of parallel, narrow and long microchannels. Each microchannel section may include one or more microchannels (e.g. two, three, four, five or any higher number of microchannels). A well, reservoir or chamber may be provided in between respective microchannels of two sequential or adjacent microchannel sections. In various embodiments, each individual section of microchannels may have at least substantially similar channels (e.g. in terms of dimensions), and may be coupled and/or connected to a well, which in turn is coupled and/or connected to the subsequent microchannel section, in the upstream and/or downstream direction. The width of each microchannel and/or the number of the microchannels in a microchannel section may be larger than that of the respective in the downstream direction subsequent microchannel section from the input reservoir to the output reservoir. In other words, the width of each microchannel and/or the number of the microchannels in a microchannel section may progressively decrease from one microchannel section to the subsequent microchannel section in the downstream direction. In various embodiments, the spermatozoa experience two-dimensional confinement in their transit through the plurality of microchannel sections.

It should be appreciated that the structured 'confinement gradients' of 2-D confinement may be extended to provide 3-D confinement where the depth or height of each microchannel in a microchannel section may be larger than that of the respective in the downstream direction subsequent microchannel section. In other words, the depth of each microchannel in a microchannel section may progressively decrease from one microchannel section to the subsequent microchannel section in the downstream direction.

In various embodiments, the structured 'confinement gradients' may include 1-D confinement, for example due to wide and thin microchannels or microchannel 'slits'. As an example and not limitations, the input reservoir and the output reservoir may be joined, coupled and/or in fluid communication with a series of slits (e.g. sequential slits) of progressively decreasing height (micrometer scale).

In the context of various embodiments, the specific architectural details of the configuration of each structured confinement gradient, for example the channel dimensions, the number of microchannel sections, the number of microchannels in each microchannel section, etc., may be optimized to enable separation of a target number of sperm of required motility from the original sample.

Various embodiments may provide passive microfluidic devices and a method of forming or fabrication of passive microfluidic devices for the isolation of motile/healthy spermatozoa, thereby enabling the selection of viable sperm or spermatozoa, for example of defined characteristics, and which may subsequently be used for in vitro fertilization (IVF).

Various embodiments may provide a passive microfluidic device or a microchannel device for sorting of spermatozoa, for example for in vitro fertilization (IVF). A sample or a seminal fluid containing sperm or spermatozoa may be provided to the passive microfluidic device (e.g. a sperm sorter device) so as to sort, isolate or select spermatozoa that are highly motile and/or of certain defined characteristics that may be suitable for IVF. The sample or the seminal fluid may be unprocessed, as-obtained from a subject, or may be processed to at least substantially remove other cells or particles other than sperm from the sample.

In the context of various embodiments, an unprocessed sample refers to a sample as-obtained from a subject, e.g. human. The unprocessed sample may include motile spermatozoa, immotile spermatozoa, dead spermatozoa, non-germ cells, debris and seminal fluid. The seminal fluid provides a nutritive and protective medium for the spermatozoa during the fertilization process. The seminal fluid may include components such as fructose, galactose, proteolytic enzymes, amino acids, proteins, prostaglandins, flavins, zinc, citrate, acid phosphatase, fibrinolysin, prostate specific antigen, mucus, sialic acid and pre-ejaculate (preseminal fluid). A processed sample refers to a sample in which the spermatozoa may be separated from the seminal fluid for a variety of purposes such as diagnostic tests of function and/or assisted reproductive technologies. Different methods of processing a sperm sample are available to the person skilled in the art.

Various embodiments may provide a passive microfluidic device and a method of forming the same which seek to address the problems associated with conventional IVF techniques or devices, and at the same time ensures that the passive microfluidic device is low-cost (i.e. cheap) and easily reproducible. The passive microfluidic device may be used for isolating motile spermatozoa with normal morphology from unprocessed samples with oligospermic conditions for subsequent fertilization.

Various embodiments may provide a passive microfluidic device that performs passive sorting of unprocessed spermatozoa in order to reduce numerous human interventions. In addition, the passive microfluidic device may be used to mirror or mimic the in vivo conditions or natural fertilization process, equivalent of the human body, in order to reduce unnecessary stress on the gametes. Therefore, the passive microfluidic devices of various embodiments may provide a hands-free mode of sperm or spermatozoa sorting under more in vivo like conditions.

Various embodiments may provide a passive microfluidic device and a passive microfluidic device-based method for sorting and capturing motile sperm from untreated human (or animal) semen samples (e.g. untreated semen samples). In various embodiments, the method is completely passive, involves no manual intervention during the sorting process, and simply involves an initial loading of a semen sample and subsequently harvesting the sorted spermatozoa at the end of the sorting process.

Various embodiments may provide a passive microfluidic device made of polydimethysiloxane (PDMS), for example fabricated by soft lithography. The passive microfluidic device may be bonded to a glass slide. The passive microfluidic device may be developed for IVF. In various embodiments, use of this passive microfluidic device or micro-device, for example for isolation of motile sperm (i.e. spermatozoa), may reduce the need for manual handling and labor-intensive selection of healthy sperm cells for IVF.

In various embodiments, the passive microfluidic device or micro-device may include an input reservoir or input well, an output reservoir or output well, and a plurality of microchannel sections in fluid communication with each other, and connected to and/or coupled to and/or in fluid communication with the input reservoir and the output reservoir. The passive microfluidic device of various embodiments performs sorting based on volumetric confinement, where the total volume of a microchannel section progressively decreases, from one microchannel section to the subsequent microchannel section in the downstream direction, as the sperm move from the input reservoir to the output reservoir.

The plurality of microchannel sections are arranged sequentially and in fluid communication with each other between the input reservoir and the output reservoir, and designed to define a closed microchannel system between the input reservoir and the output reservoir. Each microchannel section of the plurality of microchannel sections includes at least one microchannel. In various embodiments, for each microchannel section, the total volume of the microchannels of one microchannel section is larger than that of the respective in the downstream direction subsequent microchannel section. In various embodiments, the larger total volume may be because of a larger total cross section of all microchannels in the microchannel section and/or a larger number of microchannels in the microchannel section, compared to that of the respective, in the downstream direction, subsequent microchannel section. Therefore, the sperm are progressively confined moving from one microchannel section to the subsequent microchannel section in the downstream direction. In various embodiments, one or more intermediate wells or reservoirs may be provided or formed, each well being coupled to or connected between the respective microchannels of two sequential microchannel sections.

Unprocessed sperm samples may be loaded into or through the input reservoir. Sperm swim or move through the one or more microchannels of each microchannel section to the one or more intermediate wells in a uni-directional flow from the input reservoir towards the output reservoir. As a result, only highly motile sperm may reach the output reservoir, for example due to the constrictions imposed by progressively smaller total cross section of the microchannels of each microchannel section from one microchannel section to the subsequent microchannel section in the downstream direction, for example as a result of changes in the width and/or depth of each microchannel within a microchannel section, and/or the progressively decreasing number of microchannels, from one microchannel section to the subsequent microchannel section in the downstream direction. Such constrictions may reduce the probabilities of sperm other than highly motile sperm or spermatozoa from reaching and entering narrow and/or decreased number of microchannels. In various embodiments, oocytes may be placed at the output reservoir for fertilization by the motile sperm. Other particles and/or cells that are present in the unprocessed sperm samples may be retained within the input reservoir or at least substantially within the one or more microchannels of the microchannel section immediately adjacent to the input reservoir (i.e. the first microchannel section), while the sperm move from the input reservoir to the output reservoir.

By using the passive microfluidic device of various embodiments, a lower total number, concentration and volume of flagellated cells, for example sperms, are required compared to conventional IVF procedures. In addition, the natural biological environment of fertilization is mimicked where the fittest sperm or spermatozoa may be selected based on their ability to swim or move through the microchannels of the plurality of microchannel sections to reach the oocytes, instead of by artificial manual selection.

In various embodiments, the microchannels of the passive microfluidic devices may be modified, for example surface-modified, to enable selection of sperm or spermatozoa of specific characteristics, for example sperm with no genetic mutations (i.e. absence of genetic mutations).

In order that the invention may be readily understood and put into practical effect, particular embodiments will now be described by way of examples and not limitations, and with reference to the figures.

FIG. 1 shows a schematic block diagram of a passive counter flow free microfluidic device 100 for sorting a sample of flagellated cells, according to various embodiments. The passive microfluidic device 100 includes an input reservoir 102 configured to receive the sample of flagellated cells, an output reservoir 104 positioned downstream of the input reservoir 102, the output reservoir 104 configured to collect the flagellated cells that are sorted, and a plurality of microchannel sections 106 arranged sequentially and in fluid communication with each other between the input reservoir 102 and the output reservoir 104, and designed to define a closed microchannel system between the input reservoir 102 and the output reservoir 104, wherein each microchannel section (e.g. 108, 110) comprises at least one microchannel (e.g. 112, 114), wherein an inlet of the microchannel 112 of a first microchannel section 108 of the plurality of microchannel sections 106 is connected to the input reservoir 102, wherein an outlet of the microchannel 114 of a last microchannel section 110 of the plurality of microchannel sections 106 is connected to the output reservoir 104, and wherein, for each microchannel section (e.g. 108, 110), the total volume of the microchannels (e.g. 112) of one microchannel section (e.g. 108) of the plurality of microchannel sections 106 is larger than that of the respective in said downstream direction subsequent microchannel section (e.g. 110) of the plurality of microchannel sections 106 for sorting the flagellated cells when the flagellated cells move from the input reservoir 102 to the output reservoir 104.

As an example and not limitation, in embodiments where the plurality of microchannel sections 106 includes two microchannel sections (i.e. the first microchannel section 108 and the last microchannel section 110), the total volume of the microchannel(s) 112 of the first microchannel section 108 is larger than the total volume of the microchannel(s) 114 of the last microchannel section 110.

As illustrated by 116, the input reservoir 102, the output reservoir 104 and the plurality of microchannel sections 106 are in fluid communication with each other. As illustrated by 118, the microchannel sections (e.g. the first microchannel section 108, the last microchannel section 110) are in fluid communication with each other.

While FIG. 1 shows that the plurality of microchannel sections 106 includes the first microchannel section 108 and the last microchannel section 110, it should be appreciated that the plurality of microchannel sections 106 may include any number of microchannel sections, for example two, three, four, five or any higher number of microchannel sections. The dashed line shown between the first microchannel section 108 and the last microchannel section 110 illustrates that there may be one or more intermediate microchannel sections in between the first microchannel section 108 and the last microchannel section 110. In various embodiments, the plurality of microchannel sections 106 may include two microchannel sections (i.e. the first microchannel section 108 and the last microchannel section 110). In various embodiments, the plurality of microchannel sections 106 may include more than two microchannel sections, thereby including the first microchannel section 108, the last microchannel section 110 and one or more intermediate microchannel sections in between the first microchannel section 108 and the last microchannel section 110.

In the context of various embodiments, the term "passive counter flow free microfluidic device" means a microfluidic device that operates passively, and without the need of a driving force, for example to drive the flagellated cells (e.g. sperm), for sorting the flagellated cells. In addition, the term also means that the microfluidic device has a counter flow free operation, where the passive counter flow free microfluidic device may sort the flagellated cells without the need for the flagellated cells to move against a direction of flow of a fluid, for example. In other words, the flagellated cells may be sorted via volumetric confinement and intrinsic motility differences, without the need to provide a counter flow fluid, where the counter flow fluid may generate a flow field against the direction of motion of the flagellated cells.

In the context of various embodiments, the flagellated cells may include self-propelled and/or motile cells (e.g. single-celled organisms), such that for example the flagellated cells are motile. Therefore, the passive counter flow free microfluidic device 100 may be utilized or employed for sorting a sample of self-propelled and/or motile cells.

In the context of various embodiments, the term "sequentially" as applied to the plurality of microchannel sections means that individual microchannel sections are arranged one after the other.

In the context of various embodiments, the term "first microchannel section" means the microchannel section immediately adjacent to and connected to the input reservoir. The first microchannel section is in fluid communication with the input reservoir.

In the context of various embodiments, the term "last microchannel section" means the microchannel section immediately adjacent to and connected to the output reservoir, in the downstream direction of the input reservoir. The last microchannel section is in fluid communication with the output reservoir.

In the context of various embodiments, the term "closed microchannel system" means a microchannel system where the microchannels may not be accessible other than by way of the input reservoir and/or the output reservoir. In other words, there are no intervening or intermediate structures that are coupled to or connected to any point of the close microchannel system that may allow access to the microchannels of the plurality of microchannel sections within the closed microchannel system. Therefore, any sample of flagellated cells or any fluid (e.g. a cleaning fluid or a buffer solution) may only be provided to the microchannels of the closed microchannel system via the input reservoir and/or the output reservoir.

In the context of various embodiments, the term "total volume" as applied to the microchannels of one microchannel section means the sum of the respective volumes of each microchannel in that microchannel section. As examples and not limitations, where the microchannel section includes a microchannel, the total volume is the volume of the single microchannel. Where the microchannel section includes two microchannels, the total volume is the sum of the respective volumes of the two microchannels. The volume of a microchannel may be defined as (width×depth×length) of the microchannel.

In other words, the total volume of a microchannel section may be defined by the volume of each microchannel section (i.e. length, width and depth) and the number of the microchannel(s) in the microchannel section. As an example and not limitation, where a first microchannel section includes five microchannels and a second microchannel section includes three microchannels, and where each microchannel of the first microchannel section and the second microchannel section has at least substantially same cross section (i.e. width and depth) and length, the total volume of the first microchannel section is larger than the total volume of the second microchannel section due to the higher number of microchannels in the first microchannel section.

Therefore, in various embodiments, for each microchannel section, the total volume of the microchannels of one microchannel section may changed by changing the cross section (e.g. width and/or depth) of the microchannels of that microchannel section and/or changing the number of microchannels of that microchannel section.

In various embodiments, the respective microchannels of the plurality of microchannel sections 106 may form at least one continuous microchannel. For example, the microchannel 112 and the microchannel 114 may form at least one continuous microchannel. In other words, the microchannel 112 and the microchannel 114 are part of the at least one continuous microchannel or that at least one continuous microchannel may be provided such that a part of the at least one continuous microchannel may be designated as the microchannel 112 and another part designated as the microchannel 114, the microchannel 114 being continuous and in fluid communication with the microchannel 112.

In various embodiments, the first microchannel section 108 may include a plurality of spaced apart microchannels, for example two, three, four, five, six or any higher number of microchannels.

In various embodiments, each microchannel section (e.g. 108, 110) may include a plurality of spaced apart microchannels (for example two, three, four, five, six or any higher number of microchannels).

In various embodiments, where each microchannel section (e.g. 108, 110) includes a plurality of spaced apart microchannels, the number of the plurality of spaced apart microchannels of one microchannel section is larger than that of the respective in the downstream direction subsequent microchannel section. For example, the first microchannel section 108 may include a plurality of spaced apart microchannels and the last microchannel section 110 may include a plurality of spaced apart microchannels, where the number of the microchannels in the first microchannel section 108 is larger than the number of the microchannels in the last microchannel section 110. In the context of various embodiments, the number of microchannel sections of the respective set of at least one microchannel section progressively decreases in the downstream direction (i.e. from the input reservoir to the output reservoir). This may allow sorting of flagellated cells, in particular sorting of highly motile spermatozoa. As a result, only highly motile sperm may reach the output reservoir due to the reduction in the number of microchannels, as such an arrangement may reduce the probabilities of sperm other than highly motile sperm or spermatozoa from reaching and entering the reduced number of microchannels and reach the output reservoir.

In the context of various embodiments, the term "spaced apart" as applied to the plurality of microchannels may mean that adjacent microchannels may be separated by a gap. The plurality of microchannels may be arranged in parallel to each other or may be arranged spaced apart at one end of the microchannels (e.g. respective inputs of the microchannels) and converging towards each other at the opposite end (e.g. respective outputs of the microchannels), with or without being spaced apart at the output end.

In various embodiments, for each microchannel section, the total cross section of all microchannel(s) of one microchannel section may be larger than that of the respective in the downstream direction subsequent microchannel section. For example, the total cross-section of all the microchannel(s) (e.g. 112) of the first microchannel section 108 may be larger than the total cross-section of all the microchannel(s) (e.g. 114) of the last microchannel section 110. This may allow sorting of flagellated cells, in particular sorting of highly motile spermatozoa from a sample of sperm cells as the motile spermatozoa move in the downstream direction from the input reservoir to the output reservoir. Therefore, where a sample of sperm cells is provided to the input reservoir, the sample may include spermatozoa (motile sperm cells) and spermatia (non-motile sperm cells). As the spermatozoa move in the downstream direction from the input reservoir to the output reservoir, only the highly motile spermatozoa are able to move through and be guided by the microchannels to reach the output reservoir, while the non-motile spermatozoa or spermatozoa with normal motility may face challenges in trying to reach the output reservoir due to the decreased total cross sections of microchannel(s) of the respective microchannel sections in the downstream direction. Therefore, the highly motile spermatozoa may be sorted from the sample of sperm cells.

In the context of various embodiments, the term "total cross section" as applied to the microchannels of one microchannel section means the sum of the respective cross sections of each microchannel in that microchannel section. As examples and not limitations, where the microchannel section includes a microchannel, the total cross section is the cross section of the single microchannel. Where the microchannel section includes two microchannels, the total cross section is the sum of the respective cross sections of the two microchannels. The cross section of a microchannel may be defined as (width×depth) of the microchannel.

In various embodiments, for each microchannel section, the total cross section of all microchannels of one microchannel section may changed by changing the width and/or depth of all the microchannels of that microchannel section or changing the width and/or depth of individual microchannels of that microchannel section.

In various embodiments, for each microchannel section, the cross section and/or width and/or depth and/or length of each microchannel may be at least substantially same or may be different.

In various embodiments, the cross section and/or width and/or depth and/or length of each microchannel of a microchannel section may be at least substantially same or different than that of another microchannel section.

In various embodiments, the total cross section of all microchannels of a microchannel section may be at least substantially same or different than that of another microchannel section. For example, the total cross section of all microchannels of a microchannel section may be equal to or larger than the total cross section of all microchannels of a subsequent microchannel section in the downstream direction.

In various embodiments, the number of microchannels of a microchannel section may be at least substantially same or different than that of another microchannel section. For example, the number of microchannels of a microchannel section may be equal to or larger than the number of microchannels of a subsequent microchannel section in the downstream direction. As an example and not limitation, in the downstream direction from the input reservoir 102 to the output reservoir 104 through the microchannels of the first microchannel section 108, an intermediate microchannel section and the last microchannel section 110, the number of microchannels (e.g. 112) of the first microchannel section 108 may be more than or equal to the number of microchannels of the intermediate microchannel section and in turn, the number of microchannels of the intermediate microchannel section may be more than or equal to the number of microchannels (e.g. 114) of the last microchannel section 110. Therefore, in various embodiments, the number of microchannels of sequential microchannel sections may progressively decrease in the downstream direction from a microchannel section to a subsequent microchannel section.

In various embodiments, for each microchannel section, the width of each microchannel may be at least substantially same along a length of each microchannel. In other words, the width of each microchannel may be consistent or substantially consistent along the length of each microchannel. For example, the width of each microchannel of the at least one microchannel 112 may be at least substantially same along a length of each microchannel.

In various embodiments, for each microchannel section, the width of each microchannel may be between about 2 μm and 1 cm. In various embodiments, the width of each microchannel of the first microchannel section 108 may be between about 100 μm and about 1 cm.

In various embodiments, the width of each microchannel of the last microchannel section 110 may be between about 2 μm and about 20 μm. The width of each microchannel of the last microchannel section 110 may be comparable to the cross-sectional size of a single cell of the flagellated cells to be sorted, such that, for example, highly motile sperm may be able to enter the microchannel and pass therethrough while non-motile sperm may encounter challenges, due to the narrow width, in trying to enter the microchannel and pass therethrough.

In various embodiments, for each microchannel section, the depth of each microchannel may be at least substantially same along a length of each microchannel. In other words, the depth of each microchannel may be consistent or substantially consistent along the length of each microchannel. For example, the depth of each microchannel of the at least one microchannel 112 may be may be at least substantially same along a length of each microchannel.

In various embodiments, for each microchannel section, the depth of each microchannel may be between about 2 μm and about 500 μm.

In various embodiments, the depth of each microchannel of the last microchannel section 110 may be between about 2 μm and about 20 μm. The depth of each microchannel of the last microchannel section 110 may be comparable to the cross-sectional size of a single cell of the flagellated cells to be sorted, such that, for example, highly motile sperm may be able to enter the microchannel and pass therethrough while non-motile sperm may encounter challenges, due to the smaller depth, in trying to enter the microchannel and pass therethrough.

In various embodiments, a respective well (e.g. a respective intermediate well) may be connected between the respective microchannels of two sequential microchannel sections of the plurality of microchannel sections 106. Each respective well may have a diameter of between about 5 mm and about 10 cm. The respective well is in fluid communication with the plurality of microchannel sections 106, the input reservoir 102 and the output reservoir 104.

For example, in embodiments including two microchannel sections (i.e. the first microchannel section 108 and the last microchannel section 110), a well (e.g. an intermediate well) may be formed and/or connected between the first microchannel section 108 and the last microchannel section 110, where an outlet of the microchannel (e.g. 112) of the first microchannel section 108 may be connected to the well, and an inlet of the microchannel (e.g. 114) of the last microchannel section 110 may be connected to the well. The well may have a diameter of between about 5 mm and about 10 cm.

In embodiments where the plurality of microchannel sections 106 may include the first microchannel section 108, the last microchannel section 110 and an intermediate microchannel section formed and/or arranged in between the first microchannel section 108 and the last microchannel section 110, a first well (e.g. a first intermediate well) may be formed and/or connected between the first microchannel section 108 and the intermediate microchannel section and/or a second well (e.g. a second intermediate well) may be connected between the intermediate microchannel section and the last microchannel section 110. An outlet of the microchannel (e.g. 112) of the first microchannel section 108 may be connected to the first well and an inlet of the microchannel of the intermediate microchannel section may be connected to the first well. An outlet of the microchannel of the intermediate microchannel section may be connected to the second well and an inlet of the microchannel (e.g. 114) of the last microchannel section 110 may be connected to the second well. The first well and/or the second well may have a diameter of between about 5 mm and about 10 cm.

In various embodiments, the first well is in fluid communication with the plurality of microchannel sections 106, the input reservoir 102 and the output reservoir 104. In various embodiments, the second well is in fluid communication with the plurality of microchannel sections 106, the input reservoir 102 and the output reservoir 104.

In various embodiments, a width of the microchannel of the intermediate microchannel section may be between about 20 µm and about 100 µm.

In various embodiments, a surfactant may be coated on an inner surface of at least one of the respective microchannels of the plurality of microchannel sections. For example, a surfactant may be coated on an inner surface of the microchannel 112 of the first microchannel section 108 and/or an inner surface of the microchannel 114 of the last microchannel section 110. In various embodiments, a surfactant may also be coated on an inner surface of microchannel(s) of an intermediate microchannel section.

In various embodiments, the surfactant may include at least one hydroxyl group. This may improve the hydrophilicity and/or biocompatibility of the inner surface of the microchannels. In other words, the surfactant when coated may create a substantially hydrophilic inner surface of the microchannels.

The surfactant may be an alcohol, for example a polyol.

In various embodiments, the surfactant may be conductive and/or ionic.

It should be appreciated that examples as described above in the context of the first microchannel section 108 and the last microchannel section 110 may be correspondingly applied and/or modified for embodiments including one or more intermediate microchannel sections between the first microchannel section 108 and the last microchannel section 110.

In the context of various embodiments, the difference in the total volume of the microchannels of one microchannel section compared to that of the respective subsequent microchannel section in the downstream direction may be due to a difference in the total cross section of the microchannels of the respective microchannel sections, and/or a difference in the respective number of microchannels of the respective microchannel sections.

Figure 2:
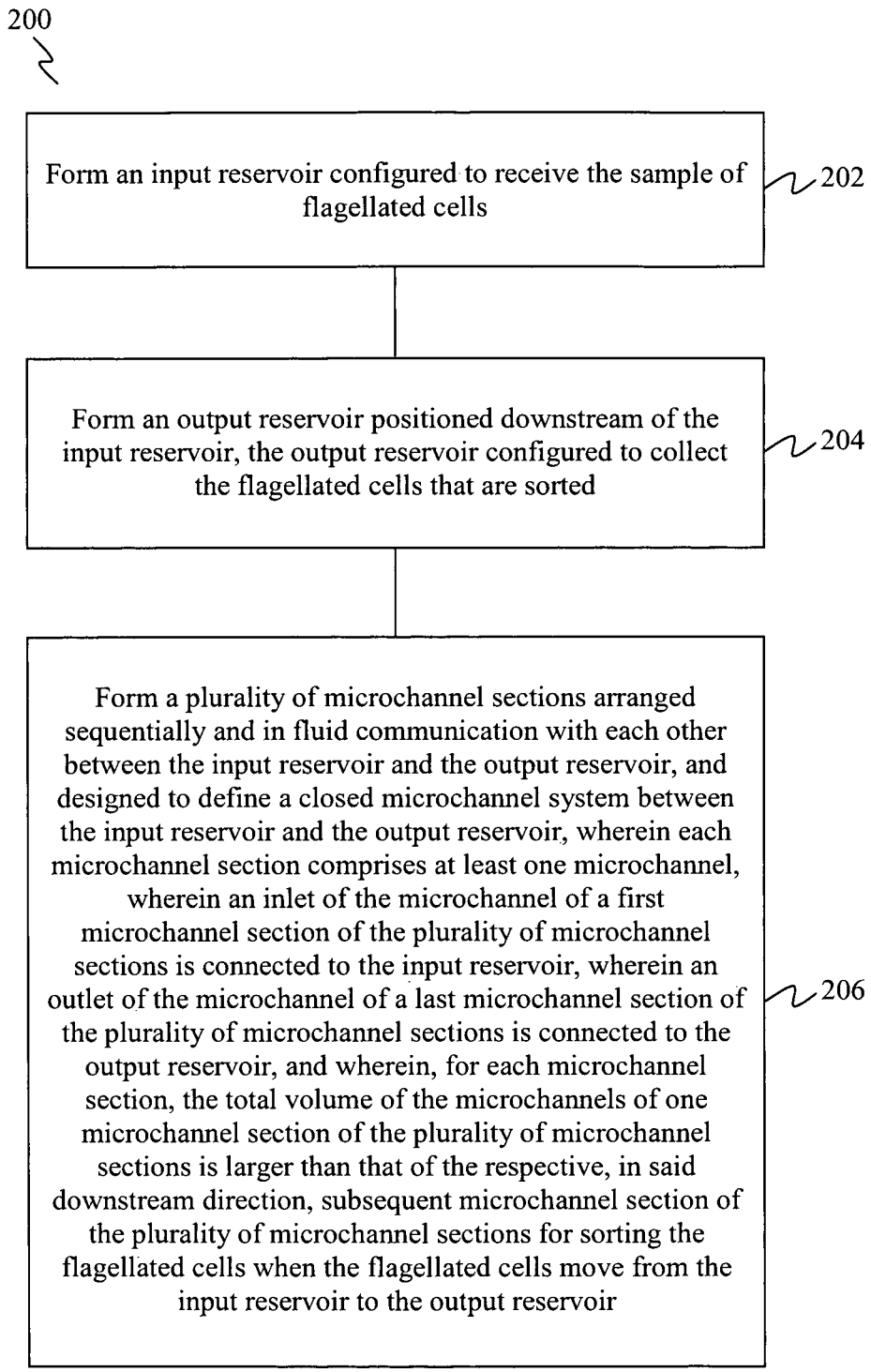
FIG. 2 shows a flow chart illustrating a method of forming a passive counter flow free microfluidic device for sorting a sample of flagellated cells, according to various embodiments.

FIG. 2 shows a flow chart 200 illustrating a method of forming a passive counter flow free microfluidic device for sorting a sample of flagellated cells, according to various embodiments.

At 202, an input reservoir configured to receive the sample of flagellated cells is formed.

At 204, an output reservoir positioned downstream of the input reservoir is formed, the output reservoir configured to collect the flagellated cells that are sorted.

At 206, a plurality of microchannel sections arranged sequentially and in fluid communication with each other between the input reservoir and the output reservoir is formed, where the plurality of microchannel sections are designed to define a closed microchannel system between the input reservoir and the output reservoir, wherein each microchannel section comprises at least one microchannel, wherein an inlet of the microchannel of a first microchannel section of the plurality of microchannel sections is connected to the input reservoir, wherein an outlet of the microchannel of a last microchannel section of the plurality of microchannel sections is connected to the output reservoir, and wherein, for each microchannel section, the total volume of the microchannels of one microchannel section of the plurality of microchannel sections is larger than that of the respective in said downstream direction subsequent microchannel section of the plurality of microchannel sections for sorting the flagellated cells when the flagellated cells move from the input reservoir to the output reservoir.

In various embodiments, the method may further include forming a plurality of spaced apart microchannels in the first microchannel section.

In various embodiments, the method may further include forming a plurality of spaced apart microchannels in each microchannel section. In various embodiments, for each microchannel section, the number of the plurality of spaced apart microchannels of one microchannel section may be larger than that of the respective in the downstream direction subsequent microchannel section.

In various embodiments, the total cross section of all microchannels of one microchannel section may be larger than that of the respective in the downstream direction subsequent microchannel section.

In various embodiments, for each microchannel section, the width of each microchannel may be at least substantially same along a length of each microchannel. For each microchannel section, the width of each microchannel may be between about 2 µm and 1 cm. The width of each microchannel of the first microchannel section may be between about 100 µm and about 1 cm. The width of each microchannel of the last microchannel section may be between about 2 µm and about 20 µm.

In various embodiments, for each microchannel section, the depth of each microchannel may be at least substantially same along a length of each microchannel. For each microchannel section, the depth of each microchannel may be between about 2 µm and about 500 µm. In various embodiments, the depth of each microchannel of the last microchannel section may be between about 2 µm and about 20 µm.

In various embodiments, the method may further include forming a respective well connected between the respective microchannels of two sequential microchannel sections of the plurality of microchannel sections.

In various embodiments, the method may include forming two microchannel sections, the two microchannel sections including the first microchannel section and the last microchannel section. The method may further include forming a well between the first microchannel section and the last microchannel section, wherein an outlet of the microchannel of the first microchannel section may be connected to the well, and wherein an inlet of the microchannel of the last microchannel section may be connected to the well. The well may have a diameter of between about 5 mm and about 10 cm.

In various embodiments, the method may include forming three microchannel sections, the three microchannel sections including the first microchannel section, the last microchannel section, and an intermediate microchannel section arranged in between the first microchannel section and the last microchannel section. A width of the microchannel of the intermediate microchannel section may be between about 20 µm and about 100 µm.

The method may further include forming a first well between the first microchannel section and the intermediate microchannel section, wherein an outlet of the microchannel of the first microchannel section may be connected to the first well, and wherein an inlet of the microchannel of the intermediate microchannel section may be connected to the first well. The method may further include forming a second well between the intermediate microchannel section and the last microchannel section, wherein an outlet of the microchannel of the intermediate microchannel section may be connected to the second well, and wherein an inlet of the microchannel of the last microchannel section may be connected to the second well. The first well and/or the second well may have a diameter of between about 5 mm and about 10 cm.

In various embodiments, the method may further include coating a surfactant on an inner surface of at least one of the respective microchannels of the plurality of microchannel sections.

In the context of various embodiments, the passive microfluidic device (e.g. 100) may be made from, but not limited to, polydimethysiloxane (PDMS) poly (N,N-dimethylacrylamide) (PDMA), polystyrene, polyethylene, polymethylmethacrylate (PMMA), cyclo-olefin polymer and quartz. However, it should be appreciated that any biocompatible material, which may be at least substantially transparent, may be used for the passive microfluidic device (e.g. 100).

In the context of various embodiments, a reference to a "passive microfluidic device" as used herein is a reference to a passive counter flow free microfluidic device.

In the context of various embodiments, the term "downstream" means a direction from the input reservoir to the output reservoir, being the direction of the motion of the flagellated cells. Conversely, the reverse direction from the output reservoir to the input reservoir is "upstream".

In the context of various embodiments, the term "well" may include a microwell, a reservoir or a recess, where the flagellated cells may be held or retained, at least temporarily, within the well due to a transit time through the well. For example in the intermediate well, the flagellated cells may experience a transit time when moving through the intermediate well in between different microchannel sections in which the intermediate well is disposed in between such that highly motile cells may be able to reach the downstream microchannel sections and the output reservoir first, thereby sorting the highly motile cells from normal motile cells, for example.

In the context of various embodiments, a reference to "spermatozoa" may include a reference to a spermatozoon.

In the context of various embodiments, a flagellated cell may refer to any cell(s) or single-cell organism(s) that has at least one tail-like projection (flagellum) protruding from the body of the cell. Examples of flagellated cells include but are not limited to spermatozoa, *Euglena, Giardia lamblia, Trichomonas vaginalis, Leishmania* spp., *Trypanosoma* spp., *Helicobacter pylori, Ceratium horridum, Ceratium furca, Ceratium tripos, Gonyaulax polyedra, Spongomonas intestinalis*, to mention only a few.

The flagellated cell can be derived from a mammal or invertebrate species, or in a microorganism. Examples of mammals include, but are not limited to a rat, a mouse, a cat, a dog, a dingo, a cow, a sheep, a horse, a pig, a goat, a chimpanzee, a macaque, and a human.

In the context of various embodiments, a culture medium containing physiologically balanced salt solutions supplemented with nutrients, suitable for the survival of sperm or oocytes, in vitro fertilization and in vitro development of the pre-implantation embryos may be provided in the passive microfluidic devices of various embodiments, for example provided at the input reservoir and/or the output reservoir.

In the context of various embodiments, the microchannel or microchannels may be at least substantially parallel to each other within the same microchannel section and/or with different microchannel sections.

In the context of various embodiments, each of the well or intermediate well may have a diameter of between about 5 mm and about 10 cm (i.e. 100 mm), for example between about 5 mm and about 50 mm, about 5 mm and about 30 mm, about 5 mm and about 10 mm or about 20 mm and about 50 mm, such that the diameter may be about 5 mm, about 10 mm, about 20 mm or about 50 mm.

In the context of various embodiments, each of the well or intermediate well may have the shape of a circle, an ellipse, a square, a rectangle, a pentagon, a hexagon or any other suitable shape. Each of the well or intermediate well may have dimensions such that the distance between adjacent or sequential microchannel sections is between about 5 mm and about 10 cm (i.e. 100 mm), for example between about 5 mm and about 50 mm, about 5 mm and about 30 mm, about 5 mm and about 10 mm or about 20 mm and about 50 mm.

In the context of various embodiments where more than one well or intermediate well is provided, different intermediate wells may have different diameters or dimensions or shapes or any combinations thereof.

In the context of various embodiments, each of the input reservoir (e.g. 102) and the output reservoir (e.g. 104) may have a diameter of between about 3 mm and about 10 cm (i.e. 100 mm), for example between about 3 mm and about 50 mm, about 3 mm and about 30 mm, about 3 mm and about 10 mm or about 20 mm and about 50 mm, such that the diameter may be about 3 mm, about 5 mm, about 10 mm, about 20 mm or about 50 mm.

In the context of various embodiments, each of the input reservoir (e.g. 102) and the output reservoir (e.g. 104) may have the shape of a circle, an ellipse, a square, a rectangle, a pentagon, a hexagon or any other suitable shape.

In the context of various embodiments, the length of each microchannel in the plurality of microchannel sections (e.g. 106) may be between about 2 mm and about 10 mm, for example between about 2 mm and about 6 mm, about 2 mm and about 4 mm, or about 5 mm and about 10 mm, such that the length may be about 2 mm, about 5 mm, or about 10 mm.

In the context of various embodiments, the width of each microchannel in the plurality of microchannel sections (e.g. 106) may be between about 2 μm and about 1 cm (i.e. 10000 μm), for example between about 2 μm and about 5000 μm, between about 2 μm and about 1000 μm, between about 2 μm and about 500 μm, between about 2 μm and about 50 μm, between about 20 μm and about 5000 μm, between about 100 μm and about 1000 μm or between about 100 μm and about 500 μm.

In the context of various embodiments, the width of each microchannel (e.g. 112) of the first microchannel section 108 may be between about 100 μm and about 1 cm (i.e. 10000 μm), for example between about 100 μm and about 5000 μm or between about 100 μm and about 1000 μm, the width of each microchannel of an intermediate microchannel section may be between about 20 μm and about 100 μm, for example between about 20 μm and about 50 μm or between about 20 μm and about 30 μm, and the width of each microchannel (e.g. 114) of the last microchannel section 110 may be between about 2 μm and about 20 μm, for example between about 2 μm and about 10 μm or between about 2 μm and about 5 μm.

However, it should be appreciated that each microchannel of the first microchannel section 108, the last microchannel section 110 and any intermediate microchannel section may have any width, such that the total volume of the microchannels of one microchannel section is larger than that of the respective subsequent microchannel section in the downstream direction.

In the context of various embodiments, the depth of each microchannel in the plurality of microchannel sections (e.g. 106) may be between about 2 µm and about 500 µm, for example between about 2 µm and about 300 µm, between about 2 µm and about 100 µm, between about 2 µm and about 50 µm, between about 2 µm and about 20 µm, between about 50 µm and about 300 µm, between about 50 µm and about 100 µm or between about 100 µm and about 300 µm.

In the context of various embodiments, the depth of each microchannel (e.g. 114) of the last microchannel section 110 may be between about 2 µm and about 20 µm, for example between about 2 µm and about 10 µm or between about 2 µm and about 5 µm.

It should be appreciated that each microchannel of the first microchannel section 108, the last microchannel section 110 and any intermediate microchannel section may have any depth, such that the total volume of the microchannels of one microchannel section is larger than that of the respective subsequent microchannel section in the downstream direction.

In the context of various embodiments, as examples and not limitations, in order to decrease the depth of the microchannel for a microchannel section in the downstream direction, microchannels of sequential microchannel sections may be micro-machined such that a microchannel in a microchannel section in the downstream direction has a depth smaller than a microchannel in a microchannel section in the upstream direction.

In the context of various embodiments, as examples and not limitations, a blocking element or structure may be positioned in a microchannel in the downstream direction, along its entire length or a portion of its length, so as to provide an effective depth that is smaller than the depth of a microchannel in a microchannel section in the upstream direction.

It should be appreciated that each microchannel of the first microchannel section 108, the last microchannel section 110 and any intermediate microchannel section may have any cross section, such that the total volume of the microchannels of one microchannel section is larger than that of the respective subsequent microchannel section in the downstream direction.

In the context of various embodiments, each microchannel (e.g. 114) of the last microchannel section 110 may have at least one cross section dimension (e.g. width and/or depth) that is comparable or at least the cross sectional size or dimension of a single cell of the flagellated cells to be sorted. As an example and not limitation, where spermatozoa are to be sorted, the width and/or depth of such a microchannel may be about 2 µm to about 2.6 µm. This may allow only the highly motile sperm to swim or move into the last microchannel section 110 and pass therethrough to reach the output reservoir 104 while non-motile sperm may encounter challenges, due to the decreased cross section (e.g. decreased width and/or depth), in trying to enter the microchannel of the last microchannel section 110 and pass therethrough to reach the output reservoir 104.

In the context of various embodiments, it should be appreciated that there may be more than three microchannel sections, i.e. the microfluidic device may have four microchannel sections, five microchannel sections or any higher number of microchannel sections. In addition, more than two intermediate wells may be provided, depending on the number of microchannel sections.

In the context of various embodiments, any combinations of decreasing total cross section of the microchannels and/or number of microchannels, from one microchannel section to a subsequent microchannel section in the downstream direction, may be provided.

In general, normal sperm motility refers to more than 50% of the spermatozoa showing normal formal movement in a given sample.

Various embodiments may further provide a method for sorting a sample of flagellated cells. The method includes supplying the sample of flagellated cells to the input reservoir of the passive microfluidic device of various embodiments.

In embodiments where the flagellated cells are spermatozoa, the method may further include providing at least one oocyte at the output reservoir of the passive microfluidic device for fertilization.

Various embodiments may further provide use of the passive microfluidic device of various embodiments for sorting spermatozoa.

In various embodiments, the passive microfluidic device may be used for sorting motile spermatozoa, for example for sorting highly motile spermatozoa from a sample containing spermatozoa.

Various embodiments may provide a passive microfluidic device that performs passive sorting of sperm and a method of sorting sperm via passive sorting. In other words, sorting of the sperm (e.g. unprocessed sperm) in various embodiments may be carried out without any driving force, in contrast to devices with active sorting where a driving force (e.g. via a pump or by hydrostatic pressure) is provided and the sperm are driven through the device by force. As an example and not limitations, in various embodiments, a medium (e.g. fluid) may be provided to an input reservoir of a passive microfluidic device, which may flow towards the output reservoir, and subsequently the medium may be in a stationary state. Then, a sample of sperm (e.g. semen) may be provided to the input reservoir of the passive microfluidic device and the sperm may swim or move from the input reservoir towards the output reservoir of the microfluidic device due to the sperm's own motive force during passive sorting.

Figure 3:
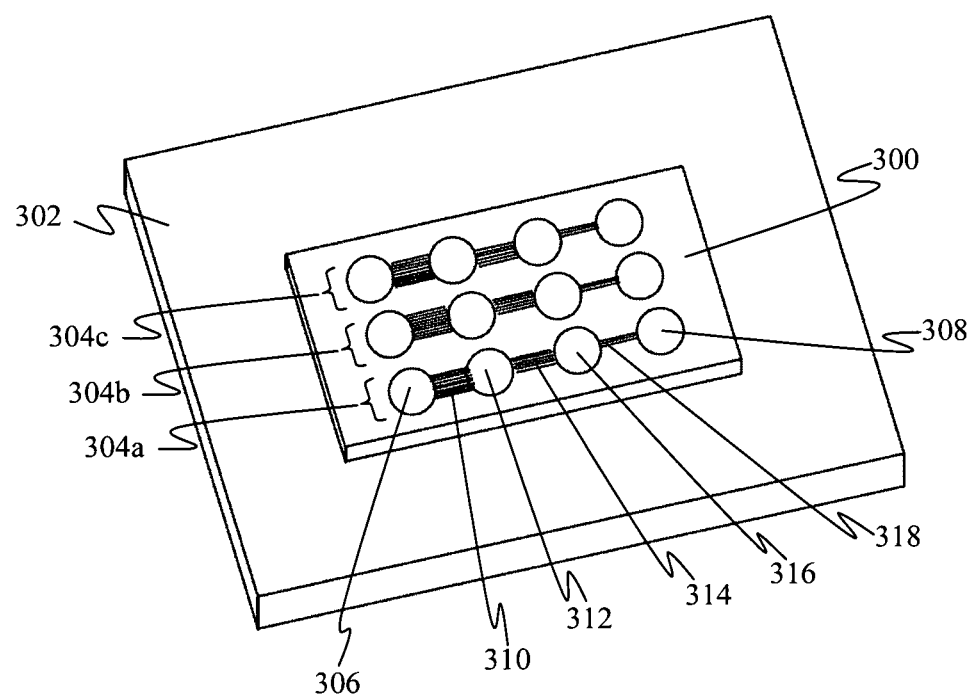
FIG. 3 shows a schematic perspective view of a passive microfluidic device, according to various embodiments.

FIG. 3 shows a schematic perspective view of a passive microfluidic device 300, according to various embodiments. The passive microfluidic device 300 may be made of a layer of PDMS and may be bonded to a layer of glass slide 302. As shown in FIG. 3, the passive microfluidic device 300 may include three row arrangements 304a, 304b, 304c, of microchannel sections including microchannels, and wells. However, it should be appreciated that the microfluidic device 300 may have any number of arrangements of microchannel sections and wells, for example one, two, three, four, five or any higher number, depending on the fabrication and/or applications.

Each of the row arrangements 304a, 304b, 304c, may have the same or different arrangements, for example as shown in FIGS. 4A and 4B, 5A to 5J and 6A to 6J or any other arrangements.

Using the arrangement 304a as an example, each arrangement may include an input reservoir or an input well 306 and an output reservoir or an output well 308. Each arrangement also includes one or more microchannels in a first mircochannel section 310, a first well or first intermediate well 312, one or more microchannels in an intermediate microchannel section 314, a second well or second intermediate well 316 and one or more microchannels in a last microchannel section 318, provided or formed in between the input reservoir 306 and the output reservoir 308, and in fluid communication with each other and with the input reservoir 306 and the output reservoir 308.

Figure 4A:
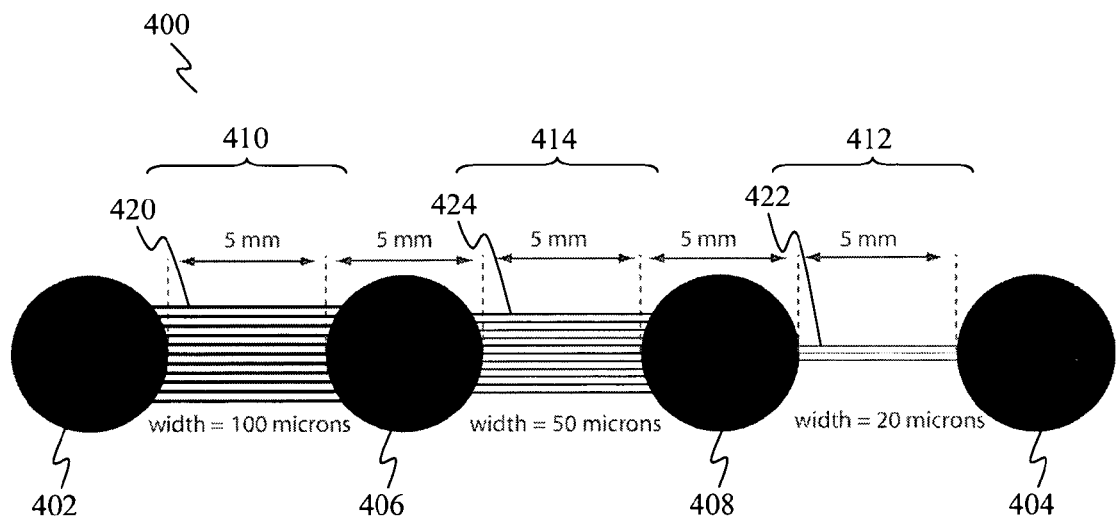
FIGS. 4A and 4B show a schematic top view and a schematic cross-sectional view, respectively, of an arrangement of microchannels and wells of a passive microfluidic device, according to various embodiments.
Figure 4B:
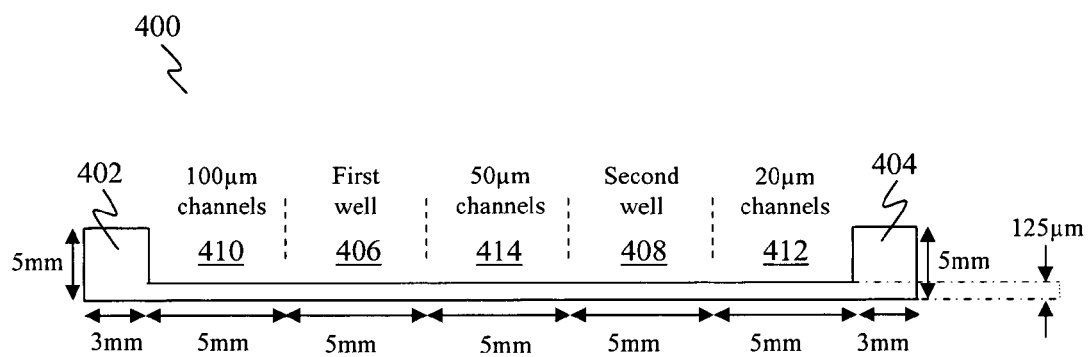
Figure 5A:
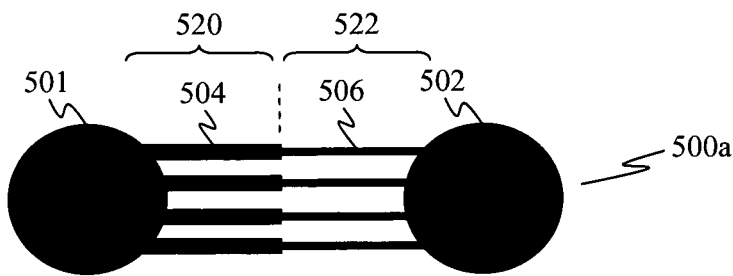
Figure 5B:
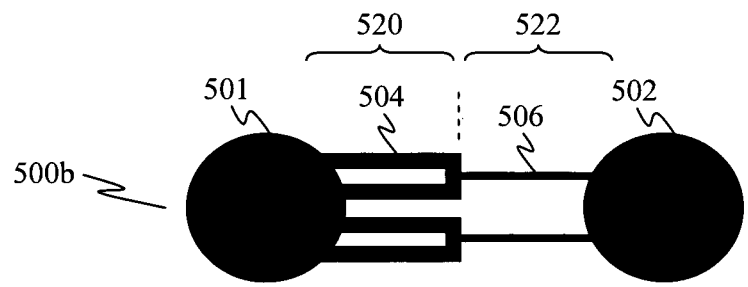
Figure 5C:
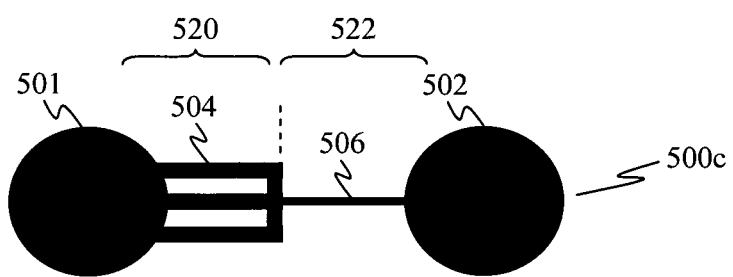
Figure 5D:
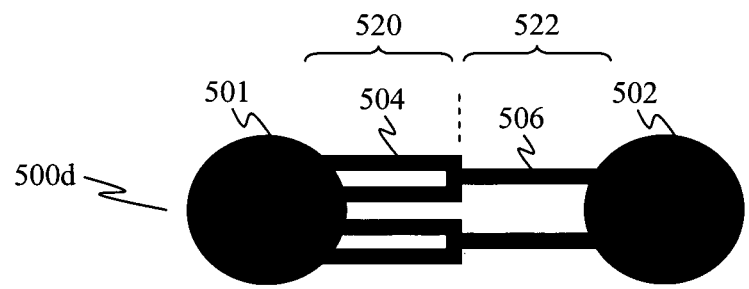
Figure 5E:
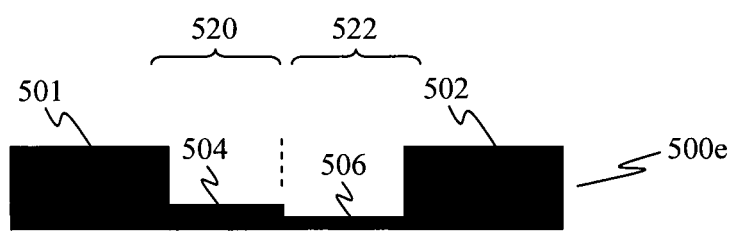
FIG. 5E shows a schematic cross-sectional view of arrangements of microchannels of a passive microfluidic device, according to various embodiments.
Figure 5F:
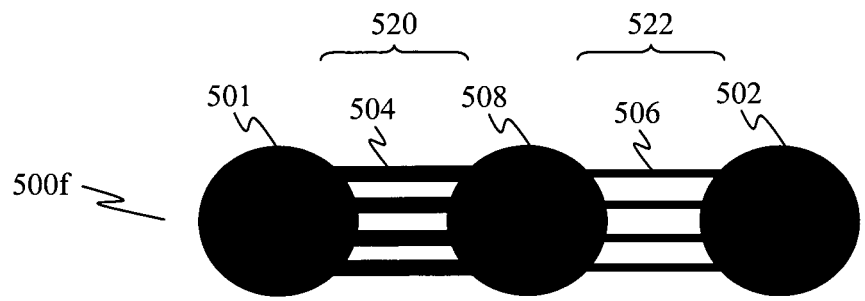
Figure 5G:
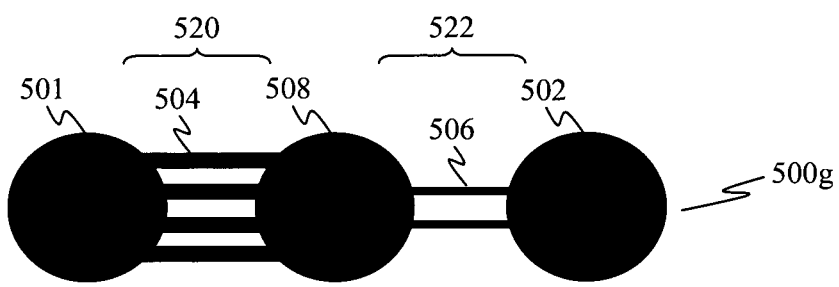
Figure 5H:
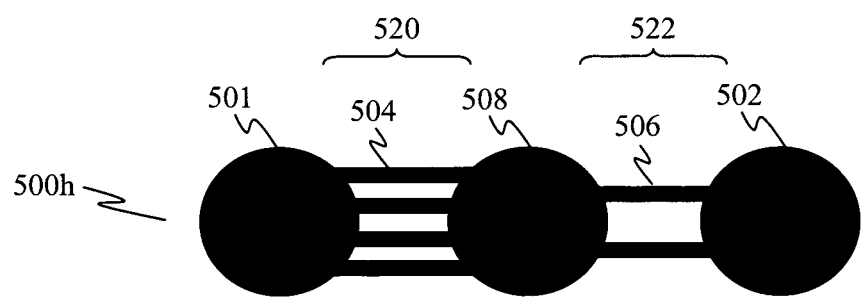
Figure 5I:
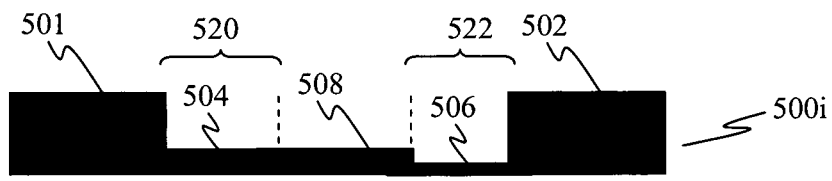
FIGS. 5I and 5J show schematic cross-sectional views of arrangements of microchannels of a passive microfluidic device, according to various embodiments.
Figure 5J:
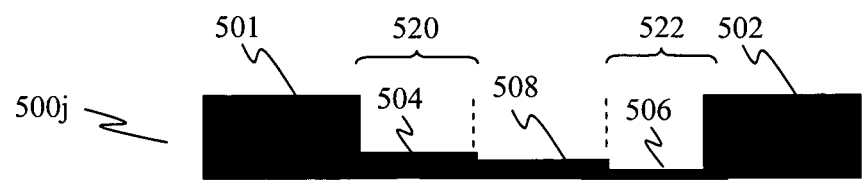
Figure 6A:
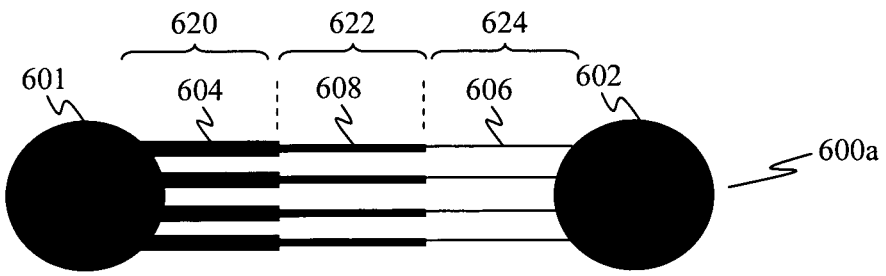
Figure 6B:
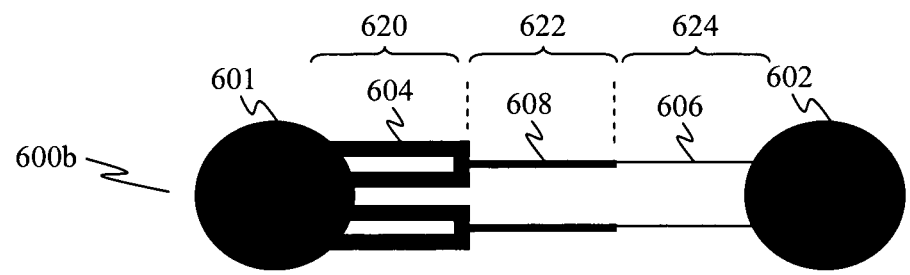
Figure 6C:
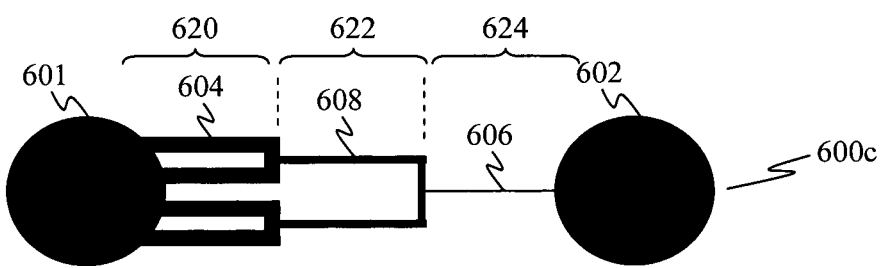
Figure 6D:
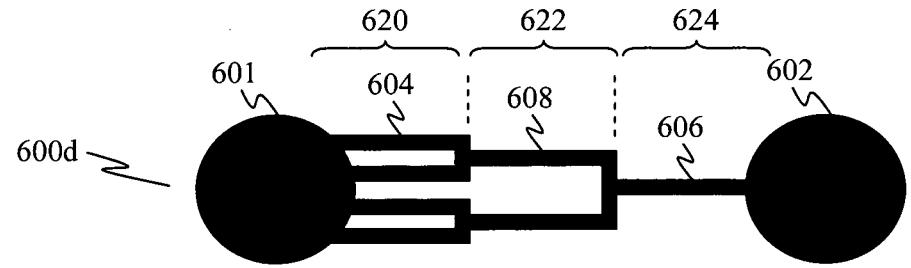
Figure 6E:
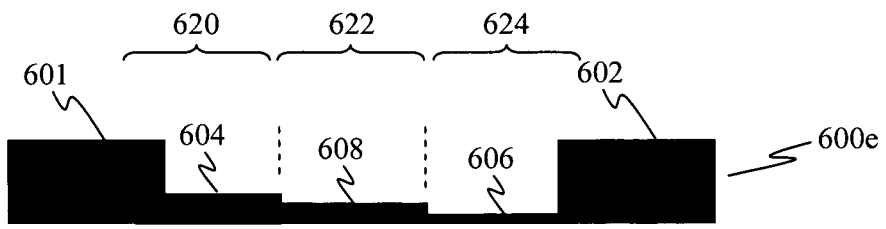
FIG. 6E shows a schematic cross-sectional view of arrangements of microchannels of a passive microfluidic device, according to various embodiments.
Figure 6F:
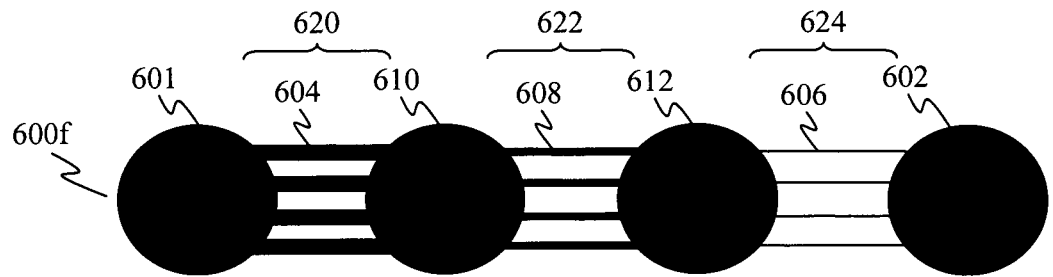
Figure 6G:
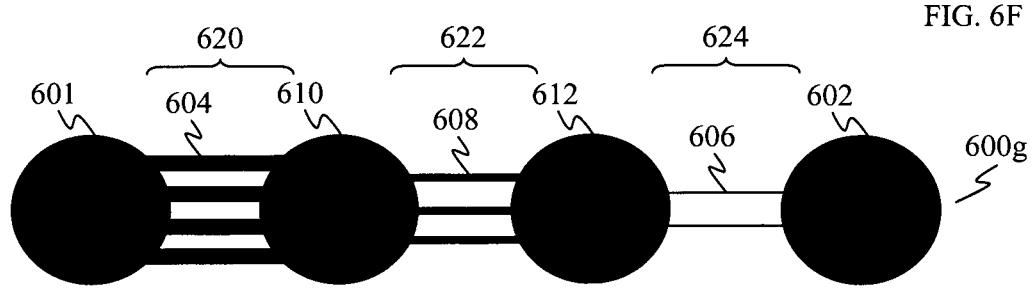
Figure 6H:
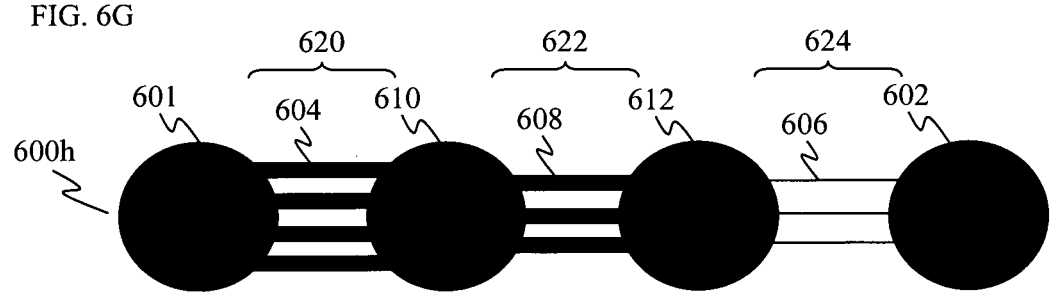
Figure 6I:
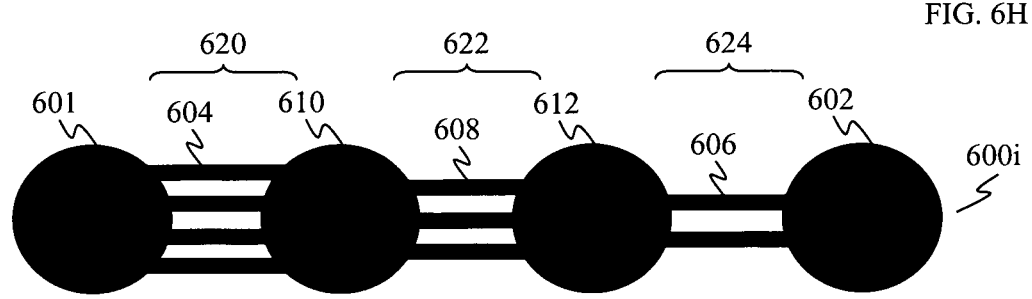
Figure 6J:
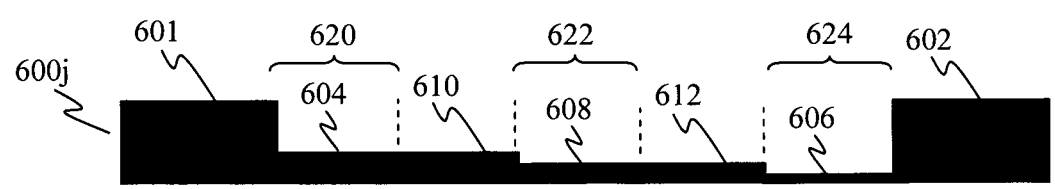
FIG. 6J shows a schematic cross-sectional view of arrangements of microchannels of a passive microfluidic device, according to various embodiments.

FIGS. 4A and 4B show a schematic top view and a schematic cross-sectional view, respectively, of an arrangement 400 of microchannels and wells of a passive microfluidic device, according to various embodiments. In FIG. 4A, dark-coloured lines are used to represent the microchannels.

The arrangement 400 of microchannels and wells includes an input reservoir 402, an output reservoir 404, a first well 406 and a second well 408. The arrangement 400 further includes a first microchannel section 410 including a plurality of microchannels, as represented by 420 for one microchannel, in between and in fluid communication with the input reservoir 402 and the first well 406 and connected to the input reservoir 402 and the first well 406. The arrangement 400 further includes a last microchannel section 412 including a plurality of microchannels, as represented by 422 for one microchannel, in between and in fluid communication with the output reservoir 404 and the second well 408 and connected to the output reservoir 404 and the second well 408. The arrangement 400 further includes an intermediate microchannel section 414 including a plurality of microchannels, as represented by 424 for one microchannel, in between and in fluid communication with the first well 406 and the second well 408 and connected to the first well 406 and the second well 408.

As shown in FIG. 4A, respective inlets of the microchannels 420 of the first microchannel section 410 are connected to the input reservoir 402 while the respective outlets of the microchannels 420 of the first microchannel section 410 are connected to the first well 406. Respective inlets of the microchannels 424 of the intermediate microchannel section 414 are connected to the first well 406 while the respective outlets of the microchannels 424 of the intermediate microchannel section 414 are connected to the second well 408. Respective inlets of the microchannels 422 of the last microchannel section 412 are connected to the second well 408 while the respective outlets of the microchannels 422 of the last microchannel section 412 are connected to the output reservoir 404.

In various embodiment, the total volume of the microchannels 420 of the first microchannel section 410 is larger than that of the intermediate microchannel section 414, which in turn is larger than that of the last microchannel section 412. In various embodiments, this may be because the number of the plurality of microchannels 420 is larger than the number of the plurality of microchannels 424 and/or the total cross section of the plurality of microchannels 420 is larger than the total cross section of the plurality of microchannels 424, and that the number of the plurality of microchannels 424 is larger than the number of the plurality of microchannels 422 and/or the total cross section of the plurality of microchannels 424 is larger than the total cross section of the plurality of microchannels 422.

As shown in FIG. 4A, the number of the microchannels 422 is less than the number of the microchannels 420 and the microchannels 424.

It should be appreciated that the input reservoir 402, the output reservoir 404, the first well 406, the second well 408, the plurality of microchannels 420, 422, 424, are in fluid communication with each other.

In various embodiments, the first well 406 and the second well 408 may be formed as recesses in the passive microfluidic device.

It should be appreciated that adjacent microchannels (e.g. 420, 422, 424) within each microchannel section (e.g. 410, 412, 414) may have any separation distance or gap.

As shown in FIGS. 4A and 4B, each of the input reservoir 402 and the output reservoir 404 has a circular shape with a diameter of approximately 3 mm and a height (or depth) or approximately 5 mm. However, it should be appreciated that the diameter of each of the input reservoir 402 and the output reservoir 404 may be between about 3 mm and about 10 cm and that the height of each of the input reservoir 402 and the output reservoir 404 may be between about 1 mm and about 10 mm, for example between about 1 mm and about 5 mm or about 3 mm and about 6 mm. In addition, it should be appreciated that the input reservoir 402 and the output reservoir 404 may be of other shapes and dimensions and that each of the input reservoir 402 and the output reservoir 404 may be of different shapes and/or dimensions.

As shown in FIGS. 4A and 4B, each of the first well 406 and the second well 408 has a circular shape with a diameter of approximately 5 mm. However, it should be appreciated that the first well 406 and the second well 408 may be of other shapes and dimensions and that each of the first well 406 and the second well 408 may be of different shapes and/or dimensions.

As shown in FIGS. 4A and 4B, the respective lengths of the plurality of microchannels 420, the plurality of microchannels 422 and the plurality of microchannels 424 are approximately 5 mm. However, it should be appreciated that any lengths may be provided and that the respective lengths of the plurality of microchannels 420, the plurality of microchannels 422 and the plurality of microchannels 424 may be different.

As shown in FIGS. 4A and 4B, the width of each (single) microchannel of the plurality of microchannels 420 is approximately 100 µm, the width of each (single) microchannel of the plurality of microchannels 424 is approximately 50 µm and the width of each (single) microchannel of the plurality of microchannels 422 is approximately 20 µm.

However, it should be appreciated that each (single) microchannel of the plurality of microchannels 420, each (single) microchannel of the plurality of microchannels 422 and each (single) microchannel of the plurality of microchannels 424 may have any widths such that the total volume of the microchannels 420 of the first microchannel section 410 is larger than that of the intermediate microchannel section 414, which in turn is larger than that of the last microchannel section 412. It should be appreciated that each (single) microchannel of the plurality of microchannels 422 may have a minimum width that is comparable to the cross section size of a single cell of the flagellated cells to be sorted.

In addition, it should be appreciated that within the plurality of microchannels 420, the width of each (single) microchannel may be different. This similarly applies to the plurality of microchannels 422 and the plurality of microchannels 424.

In various embodiments, the respective width of each (single) microchannel of the plurality of microchannels 420, each (single) microchannel of the plurality of microchannels 422 and each (single) microchannel of the plurality of microchannels 424 is at least substantially same or consistent along its respective length.

However, it should be appreciated that the respective width of each (single) microchannel of the plurality of microchannels 420, each (single) microchannel of the plurality of microchannels 422 and each (single) microchannel of the plurality of microchannels 424 may vary along its respective length, for example a tapering configuration in the downstream direction.

While FIG. 4B shows that the depth of each (single) microchannel of the plurality of microchannels 420, each (single) microchannel of the plurality of microchannels 422 and each (single) microchannel of the plurality of microchannels 424 is at least substantially the same, it should be appreciated that each (single) microchannel of the plurality of microchannels 420, each (single) microchannel of the plurality of microchannels 422 and each (single) microchannel of the plurality of microchannels 424 may have any depths such that the total volume of the microchannels 420 of the first microchannel section 410 is larger than that of the intermediate microchannel section 414, which in turn is larger than that of the last microchannel section 412. In addition, it should be appreciated that each (single) microchannel of the plurality of microchannels 422 may have a minimum depth that is comparable to the cross section size of a single cell of the flagellated cells to be sorted.

While FIGS. 4A and 4B show a plurality of microchannels 420, a plurality of microchannels 422 and a plurality of microchannels 424, it should be appreciated that each of the first microchannel section 410, intermediate microchannel section 414 and last microchannel section 412 may include one microchannel.

In addition, it should be appreciated that the respective plurality of microchannels 420, plurality of microchannels 422 and plurality of microchannels 424 may have any number of microchannels such that the number of microchannels are the same among the different microchannel sections or the number of microchannels decreases from one microchannel section to the downstream microchannel section. In other words, the number of microchannel(s) of one, microchannel section may be the same or less than that of an upstream microchannel section.

In various embodiments, the number of the microchannels may progressively decrease in the downstream direction among different microchannel sections.

In various embodiments, each microchannel of the plurality of microchannels 420, each microchannel of the plurality of microchannels 422 and each microchannel of the plurality of microchannels 424 may have a height or depth of about 125 μm or less (i.e. ≤125 μm).

In various embodiments, each of the first well 406 and the second well 408 may have a height or depth of about 125 μm.

It should be appreciated that while FIGS. 4A and 4B show three microchannel sections (i.e. 410, 412, 414) and two intermediate wells (i.e. 406, 408), the arrangement 400 may have any number of microchannel sections and intermediate wells, depending on the fabrication and/or applications.

It should be appreciated that while FIGS. 4A and 4B show an input of the microfluidic device in the form of an input reservoir 402 and an output of the microfluidic device in the form of an output reservoir 404, the input and/or the output of the microfluidic device may include a recess, a tube or an access point where samples may be provided through the input to the microchannels of the plurality of microchannel sections and samples may be extracted from the output.

FIGS. 5A to 5D, FIGS. 5F to 5H, FIGS. 6A to 6D and FIGS. 6F to 6I show schematic top views, while FIGS. 5E, 5I, 5J, 6E and 6J show schematic cross-sectional views of arrangements of microchannels of a passive microfluidic device, according to various embodiments. It should be appreciated that dark-coloured lines are used to represent the microchannels and that the thickness of the lines are exaggerated for clarity purposes to illustrate the relative differences in the thickness of the microchannels between different microchannel sections, rather than illustrating the absolute thickness of the microchannels.

Each of the arrangements 500a (FIG. 5A), 500b (FIG. 5B), 500c (FIG. 5C), 500d (FIG. 5D), 500e (FIG. 5E), 500f (FIG. 5F), 500g (FIG. 5G), 500h (FIG. 5H), 500i (FIG. 5I) and 500j (FIG. 5J), includes an input reservoir 501, an output reservoir 502, a first microchannel section 520 including one or more microchannels, as represented by 504 for one microchannel, in fluid communication with and connected to the input reservoir 501 and a last microchannel section 522 including one or more microchannels, as represented by 506 for one microchannel, in fluid communication with the output reservoir 502 and the microchannels 504 of the first microchannel section 520. The total volume of the microchannels 504 of the first microchannel section 520 is larger than the total volume of the microchannels 506 of the last microchannel section 522. In various embodiments, the total volume of the microchannels 504 of the first microchannel section 520 is larger than the total volume of the microchannels 506 of the last microchannel section 522 as a result of a larger total cross section of the microchannels 504 and/or the number of the microchannels 504 as compared to the microchannels 506 of the last microchannel section 522.

For the arrangement 500a, each microchannel 504 and the corresponding microchannel 506 form a single continuous microchannel. Each microchannel 504 has a width larger than the width of each microchannel 506.

For the arrangement 500b, two microchannels 504 may be adjoined and in fluid communication with one microchannel 506. Each microchannel 504 has a width larger than the width of each microchannel 506. Such an arrangement may form a continuous configuration.

For the arrangement 500c, three microchannels 504 may be adjoined and in fluid communication with one microchannel 506. Each microchannel 504 has a width larger than the width of the microchannel 506. Such an arrangement may form a continuous configuration.

For the arrangement 500d, two microchannels 504 may be adjoined and in fluid communication with one microchannel 506. Each microchannel 504 has a width at least substantially same as the width of each microchannel 506. Such an arrangement may form a continuous configuration.

While not shown in FIGS. 5A to 5D, each microchannel section 504 may have a depth larger than or at least substantially same as the depth of each microchannel 506.

For the arrangement 500e, each microchannel 504 has a depth larger than the depth of each microchannel 506. Such an arrangement may form a continuous configuration. While not shown, the width of each microchannel 504 may be at least substantially same or larger than the width of each microchannel 506, and/or the number of the microchannels 504 may be at least substantially same or larger than the number of the microchannels 506.

For the arrangements 500f to 500j, an intermediate well 508 may be provided in between and in fluid communication with the one or more microchannels 504 of the first microchannel section 520 and the one or more microchannels 506 of the last microchannel section 522.

The intermediate well 508 may have a depth that is at least substantially same as the depth of the microchannels 504 and that is larger than the depth of the microchannels 506 (FIG. 5I), a depth that is smaller than the depth of the microchannels 504 and that is larger than the depth of the microchannels 506 (FIG. 5J) or a depth that is at least substantially the same as the depth of the microchannels 506.

Each of the arrangement 600a (FIG. 6A), 600b (FIG. 6B), 600c (FIG. 6C), 600d (FIG. 6D), 600e (FIG. 6E), 600f (FIG. 6F), 600g (FIG. 6G), 600h (FIG. 6H), 600i (FIG. 6I) and 600j (FIG. 6J), includes an input reservoir 601, an output reservoir 602, a first microchannel section 620 including one or more microchannels, as represented by 604 for one microchannel, in fluid communication with and connected to the input reservoir 601, a last microchannel section 624 including one or more microchannels, as represented by 606 for one microchannel, in fluid communication with and connected to the output reservoir 602 and an intermediate microchannel section 622 including one or more microchannels, as represented by 608 for one microchannel, in fluid communication with the microchannels 604 and the microchannels 606. The total volume of the microchannels 604 of the first microchannel section 620 is larger than the total volume of the microchannels 608 of the intermediate microchannel section 622, which is in turn larger than the total volume of the microchannels 606 of the last microchannel section 624. For example, in various embodiments, the total volume of the microchannels 604 of the first microchannel section 620 is larger than the total volume of the microchannels 608 of the intermediate microchannel section 622 as a result of a larger total cross section of the microchannels 604 and/or the number of the microchannels 604 as compared to the microchannels 608 of the intermediate microchannel section 622. This may similarly be applied to the microchannels 608 of the intermediate microchannel section 622 as compared to the microchannels 606 of the last microchannel section 624.

For the arrangement 600a, each microchannel 604 and the corresponding microchannel 608 and the corresponding microchannel 606 form a single continuous microchannel. Each microchannel 604 has a width larger than the width of each microchannel 608, which in turn is larger than the width of each microchannel 606.

For the arrangement 600b, two microchannels 604 may be adjoined and in fluid communication with one microchannel 608 and one microchannel 606. Each microchannel 604 has a width larger than the width of each microchannel 608, which in turn is larger than the width of each microchannel 606. Such an arrangement may form a continuous configuration.

For the arrangement 600c, a pair of two microchannels 604 may be adjoined and in fluid communication with one microchannel 608 and a second pair of two microchannels 604 may be adjoined and in fluid communication with another microchannel 608, where the two microchannels 608 may be further adjoined and in fluid communication with one microchannel 606. Each microchannel 604 has a width larger than the width of each microchannel 608, which in turn is larger than the width of each microchannel 606. Such an arrangement may form a continuous configuration.

For the arrangement 600d, a pair of two microchannels 604 may be adjoined and in fluid communication with one microchannel 608 and a second pair of two microchannels 604 may be adjoined and in fluid communication with another microchannel 608, where the two microchannels 608 may be further adjoined and in fluid communication with one microchannel 606. Each microchannel 604, each microchannel 608 and each microchannel 606 has at least substantially the same width. Such an arrangement may form a continuous configuration.

While not shown in FIGS. 6A to 6D, each microchannel 604 may have a depth larger than or at least substantially same as the depth of each microchannel 608 and each microchannel 608 may have a depth larger than or at least substantially same as the depth of each microchannel 606.

For the arrangement 600e, each microchannel 604 has a depth larger than the depth of each microchannel 608 and each microchannel 608 has a depth larger than the depth of each microchannel 606. Such an arrangement may form a continuous configuration. While not shown, the width of each microchannel 604 may be at least substantially same or larger than the width of each microchannel 608, and/or the width of each microchannel 608 may be at least substantially same or larger than the width of each second microchannel 606, and/or the number of the microchannels 604 may be at least substantially same or larger than the number of the microchannels 608 and/or the number of the microchannels 608 may be at least substantially same or larger than the number of the microchannels 606.

For the arrangements 600f to 600j, a first intermediate well 610 may be provided in between and in fluid communication with the one or more microchannels 604 of the first microchannel section 620 and the one or more microchannels 608 of the intermediate microchannel section 622, and a second intermediate well 612 may be provided in between and in fluid communication with the one or more microchannels 608 of the intermediate microchannel section 622 and the one or more microchannels 606 of the last microchannel section 624.

The first intermediate well 610 may have a depth that is at least substantially the same as the depth of the microchannels 604 or the microchannels 608 or in between the depth of the microchannels 604 and the depth of the microchannels 608. The second intermediate well 612 may have a depth that is at least substantially the same as the depth of the microchannels 608 or the microchannels 606 or in between the depth of the microchannels 608 and the depth of the microchannels 606.

It should be appreciated that the various arrangements illustrated in FIGS. 5A to 5J and FIGS. 6A to 6J are shown as non-limiting examples and that other arrangements or variations may be provided. For example, an additional well may be provided in the arrangement 600a (FIG. 6A), such as an intermediate well (e.g. 610) in between and in fluid communication with the one or more microchannels 604 of the first microchannel section 620 and the one or more microchannels 608 of the intermediate microchannel section 622, or an intermediate well (e.g. 612) in between and in fluid communication with the one or more microchannels 608 of the intermediate microchannel section 622 and the one or more microchannels 606 of the microchannel section 624. It should be appreciated that any combination of widths (i.e. same width or different widths), depths (i.e. same depth or different depths), and/or number of microchannels (i.e. same number or different numbers) between different microchannel sections may be provided such that the respective total volumes of different microchannel sections progressively decrease from one microchannel section to the subsequent microchannel section in the downstream direction from the input reservoir to the output reservoir.

Figure 7A:
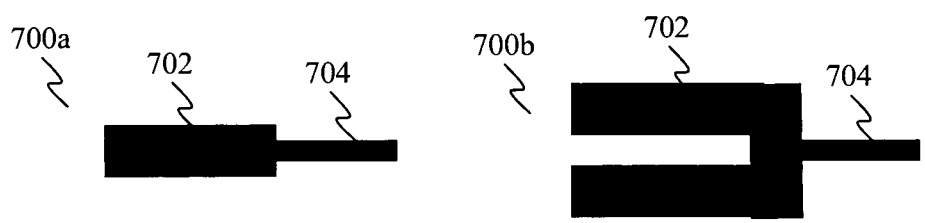
FIGS. 7A and 7B show schematic top views of intersections of microchannels between sequential microchannel sections, according to various embodiments.
Figure 7B:
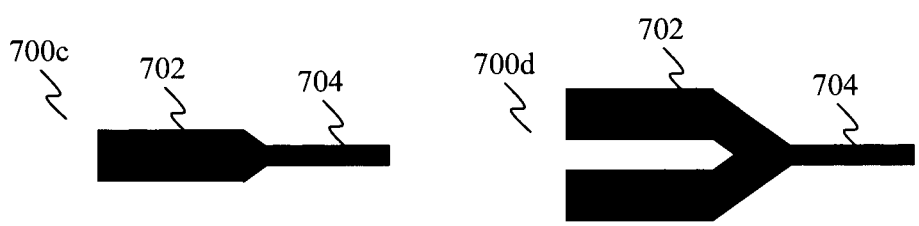

FIGS. 7A and 7B show schematic top views of intersections (or adjoining parts) 700a, 700b, 700c, 700d, of microchannels between sequential microchannel 702, 704, according to various embodiments.

As shown in FIG. 7A, the microchannels 702, 704, of sequential microchannel sections abut each other at the intersections.

As shown in FIG. 7B, the microchannel(s) 702 may be angled at the intersection to adjoin the microchannel 704. This may enable the flagellated cells to be guided as they move from the microchannel(s) 702 to the microchannel 704.

The fabrication of the passive microfluidic device will now be described below, by way of examples and not limitations.

A master silicon (Si) wafer mold may be imprinted with an SU-8 photoresist via soft lithography in order to create the suitable design or arrangement of microchannels. For creating a stamp resin, Sylgard® 184 (from DOW-Corning), a poly(dimethysiloxane) (PDMS) kit containing two parts of a liquid silicon rubber base and a curing agent, may be used. PDMS is used because of its many advantages, such as ease of fabrication, low cost, biocompatibility, elastomeric property and optical transparency, among others. In order to improve the hydrophilicity of the PDMS device, Pluronics® F127 (from Sigma-Aldrich) may be used. Pluronics® F127 is a polyol.

The Sylgard® 184 PDMS pre-polymer and its cross-linking agent (or curing agent) may be mixed in a ratio of approximately 10:1 (for example approximately 35 g:3.5 g) by mass, and degassed under vacuum. The degassed mixture is then poured over the silicon master mold and cured at about 70° C. for about 24 hours.

Subsequently, the PDMS stamp may be separated from the silicon mold and cut to fit the physical specification of the microfluidic device of, for example, approximately 45 mm×25 mm×3 mm (length×width×height). The height or thickness may be predetermined by the mass of the mixture. The input reservoir and the output reservoir of the passive microfluidic device may be manually punched out to serve as the loading and unloading reservoirs respectively.

Surface modification of the PDMS may be done by treating it with oxygen plasma in a plasma cleaner (e.g. PDC-002, Harricks Plasma) for about 45 seconds at RF high. The modified PDMS is then placed on top of a glass slide for irreversible bonding. In various embodiments, the bonding process may be by way of plasma bonding or thermal bonding.

Approximately 0.1% w/v Pluronics® F127 solution (e.g. Pluronics® crystals dissolved in approximately 10:1 of de-ionised (DI) water:phosphate buffered saline (PBS) solution) is added to the input reservoir immediately after the bonding of PDMS-glass substrate, for the surfactant coating of Pluronics® F127 in the microchannels or the inner surfaces of the microchannels. Care is taken to ensure that all the microchannels, the input reservoir and the output reservoir are filled with the Pluronics® F127 solution and that no bubbles are formed. Subsequently, the liquid-filled device may be placed in an incubator at about 37° C. and approximately 95% humidity for about 24 hours.

Subsequently, the remaining solution in the microchannels is removed and flushed with DI water. The passive microfluidic device may then be sterilized under ultra-violet (UV) light. Prior to loading of the sample of flagellated cells, for example sperm samples, the microchannels may be flushed with a proprietary flushing medium.

The study of passive flows by mammalian sperm in the microfluidic device of various embodiments will now be described below, by way of examples and not limitations.

Passive uni-directional flow in the downstream direction occurs due to the progressively increasing surface-to-volume ratio with the decreasing total volume of the microchannels of sequential microchannel sections. The passive permeation-driven flow may deliver a steady flow, for example in microchannels with the smallest volume or width, and may negate the pressure difference that may occur due to height differences of the medium or sample in the input reservoir and the output reservoir.

Approximately 1.0 µm-diameter red fluorescent polystyrene microbeads at approximately 25 vol % in deionized water may be used for visualization of the passive flows within the passive microfluidic device through the microchannels. Fluorescent microscope in green fluorescent protein (GFP) mode may be used at about 30 millisecond (i.e. 30 ms) exposure time and about 21 frames per second (fps) for observation of the bulk flow effects in the microchannels at approximately 10 second intervals for a period of about 6 hours, which is the typical time period of a standard IVF procedure. The gap average velocity may be observed, which may be extracted from tracking the small microbeads in the passive laminar flow. In order to prevent evaporation of the medium contents, a layer of paraffin oil which is biocompatible with the cell medium is placed on the exposed surfaces of the medium at the input reservoir and the output reservoir, and any intermediate wells.

Figure 8:
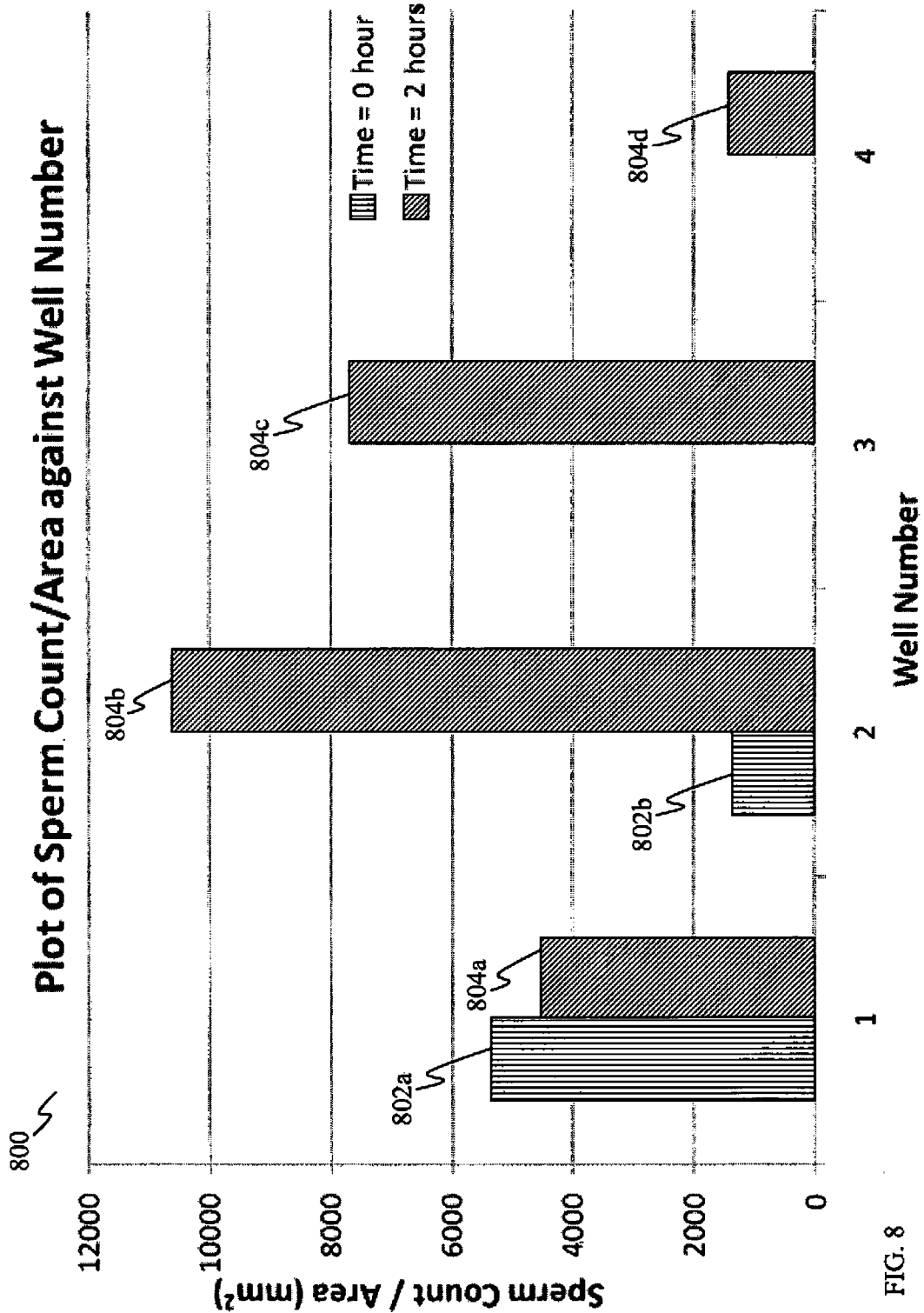
FIG. 8 shows a plot of sperm count/area ($mm^2$) in the different wells of the passive microfluidic device of various embodiments, over a period of 2 hours.

FIG. 8 shows a plot 800 of sperm count/area ($mm^2$) (e.g. sperm count per 1 $mm^2$ area) in the different wells of the passive microfluidic device of various embodiments, over a period of 2 hours. Time=0 hour refers to a time just after the initial loading of sperm to the input reservoir of the passive microfluidic device (e.g. start time). In the plot 800, well number 1 (well 1) refers to the input reservoir (e.g. FIG. 3, 306) of the passive microfluidic device, well number 2 (well 2) refers to the first intermediate well (e.g. FIG. 3, 312), well number 3 (well 3) refers to the second intermediate well (e.g. FIG. 3, 316) and well number 4 (well 4) refers to the output reservoir (e.g. FIG. 3, 308). The passive microfluidic device used to obtain the results shown in the plot 800 has well numbers 1 and 4 having larger dimensions or area than that of well numbers 2 and 3.

As shown in FIG. 8, there is no or minimal sperm count in well 3 and well 4 at 0 hour. In addition, there is an increase in the sperm count in well 2, well 3 and well 4 after 2 hours compared to time=0 hour as the sperm move from well 1 through well 2 and well 3 towards well 4.

As shown in FIG. 8, there is a decrease in the sperm count from well 2 to well 3 and to well 4 at time=2 hours, indicating a sorting event or behaviour, where only highly motile sperm are able to reach the last well (i.e. well 4).

Figure 9A:
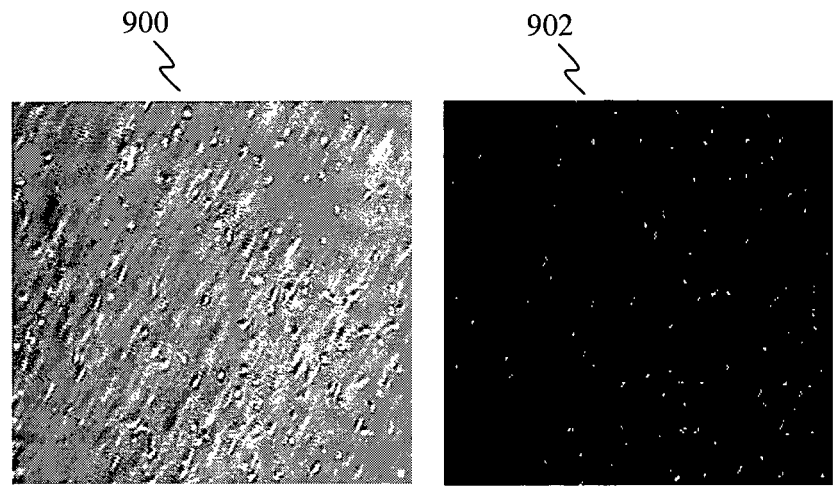
FIGS. 9A and 9B show images of sperm at time=0 hour in an input reservoir and a first intermediate well respectively of a passive microfluidic device of various embodiments.
Figure 9B:
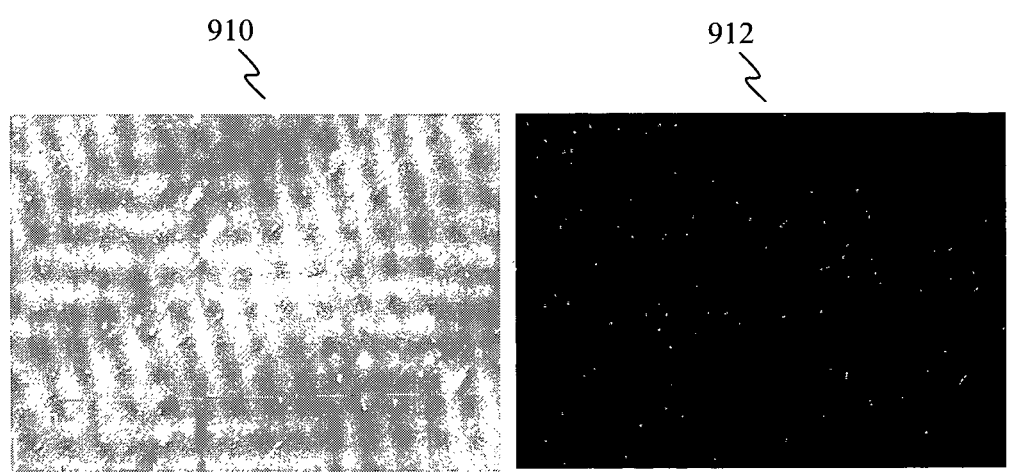

FIGS. 9A and 9B show images of sperm at time=0 hour (start time) in an input reservoir and a first intermediate well respectively of a passive microfluidic device of various embodiments. The passive microfluidic device also includes a second intermediate well and an output reservoir.

Images 900, 910, were captured from a video stream while images 902, 912, correspond to images 900, 910, respectively, after having been processed using the software MATLAB. The sperm are visible in the respective images 900, 902, 910, 912, as bright spots. While not shown, there is zero or minimal sperm count in the second intermediate well and the outlet well at time=0 hour.

FIGS. 10A, 10B, 10C and 10D show images of sperm at time=2 hours in an input reservoir, a first intermediate well, a second intermediate well and an output reservoir respectively of a passive microfluidic device of various embodiments.

Images 1000, 1010, 1020, 1030, were captured from a video stream while images 1002, 1012, 1022, 1032, correspond to images 1000, 1010, 1020, 1030, respectively, after having been processed using the software MATLAB. The sperm are visible in the respective images 1000, 1002, 1010, 1012, 1020, 1022, 1030, 1032, as bright spots.

Figure 10A:
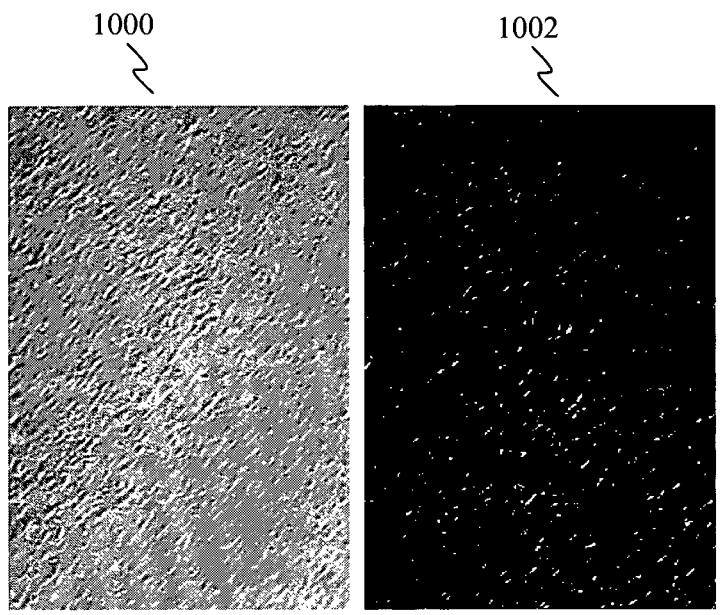
FIGS. 10A, 10B, 10C and 10D show images of sperm at time=2 hours in an input reservoir, a first intermediate well, a second intermediate well and an output reservoir respectively of a passive microfluidic device of various embodiments.
Figure 10B:
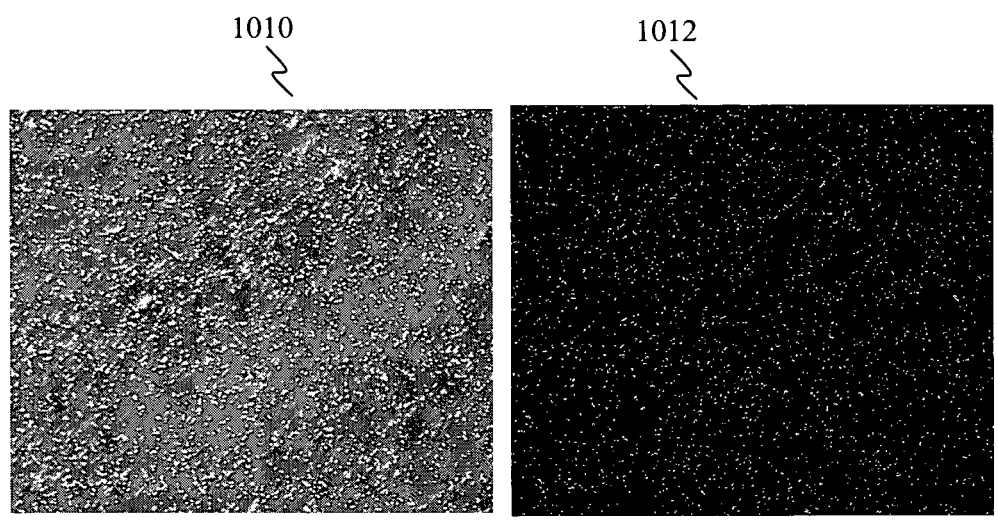
Figure 10C:
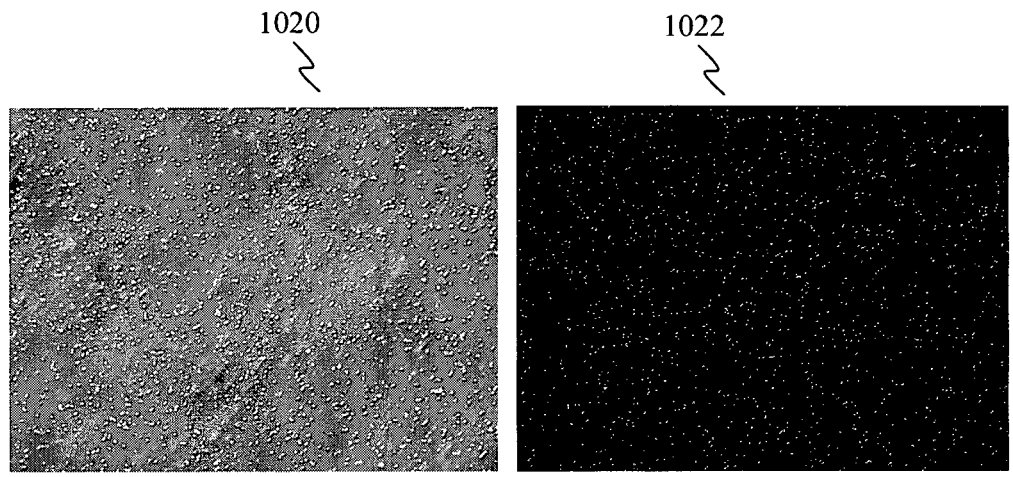
Figure 10D:
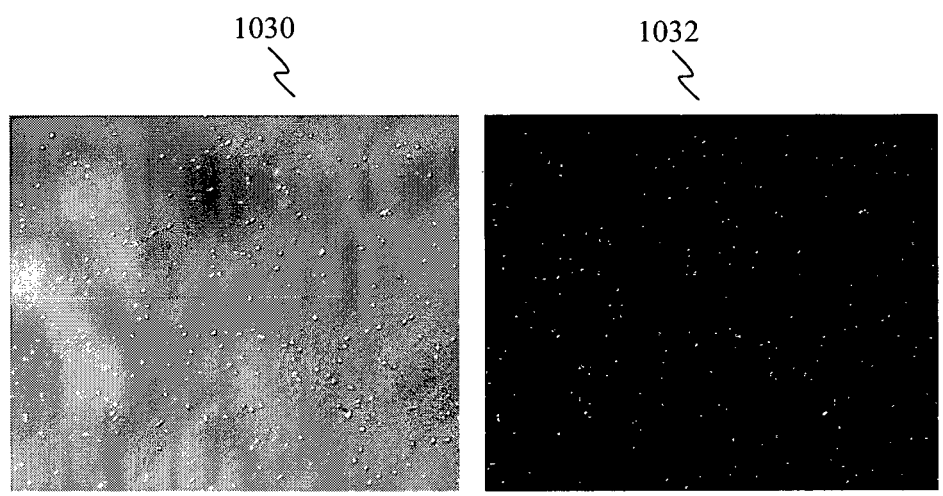

As can be seen from FIGS. 10A and 10B, there is an increase in the sperm count from the input reservoir to the first intermediate well. In addition, as can be seen from FIGS. 10B, 10C and 10D, there is a decrease in the sperm count from the first intermediate well to the second intermediate well and to the output reservoir, indicating a sorting event where only highly motile sperm are able to reach the output reservoir.

The passive microfluidic devices of various embodiments may be used in various applications for sorting flagellated cells, and in particular spermatozoa. For example, the passive microfluidic devices may be used for sorting or isolation of motile sperm (spermatozoa) from semen samples; sorting of good quality sperm with intact DNA or good sperm with DNA integrity from motile spermatozoa; and sorting of sperm with normal haploid chromosome number (e.g. 23 chromosomes in humans).

The passive microfluidic devices of various embodiments may also be used for in vitro fertilisation and in vitro embryo production.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A passive counter flow free microfluidic device for sorting a sample of flagellated cells by means of the flagellated cells' intrinsic motility difference, the passive microfluidic device comprising:
an input reservoir configured to receive the sample of flagellated cells;
an output reservoir positioned downstream of the input reservoir, the output reservoir configured to collect the flagellated cells that are sorted; and
a plurality of microchannel sections arranged sequentially and in fluid communication with each other between the input reservoir and the output reservoir, and the plurality of microchannel sections designed to define a closed microchannel system between the input reservoir and the output reservoir,
wherein each microchannel section comprises at least one microchannel,
wherein an inlet of the microchannel of a first microchannel section of the plurality of microchannel sections is connected to the input reservoir,
wherein an outlet of the microchannel of a last microchannel section of the plurality of microchannel sections is connected to the output reservoir, and
wherein, for each microchannel section, the total volume of the microchannels of one microchannel section of the plurality of microchannel sections, is larger than that of a subsequent microchannel section disposed in the downstream direction, such that the passive microfluidic device is configured to sort the flagellated cells by means of the flagellated cells' intrinsic motility difference when the flagellated cells move through a stationary fluid medium from the input reservoir to the output reservoir.

2. The passive microfluidic device as claimed in claim 1, wherein the first microchannel section comprises a plurality of spaced apart microchannels.

3. The passive microfluidic device as claimed in claim 1, wherein each microchannel section comprises a plurality of spaced apart microchannels.

4. The passive microfluidic device as claimed in claim 3, wherein for each microchannel section, the number of the plurality of spaced apart microchannels of one microchannel section is larger than that of a subsequent microchannel section disposed in the downstream direction.

5. The passive microfluidic device as claimed in claim 1, wherein for each microchannel section, the total cross section of all microchannel is larger than that of a subsequent microchannel section disposed in the downstream direction.

6. The passive microfluidic device as claimed in claim 1, wherein, for each microchannel section, the width of each microchannel is between about 2 µm and 1 cm.

7. The passive microfluidic device as claimed in claim 6, where the width of each microchannel of a first microchannel section is between 100 micron and about 1 cm.

8. The passive microfluidic device as claimed in claim 6, wherein the width of each microchannel of a last microchannel section is between about 2 microns and about 20 microns.

9. The passive microfluidic device as claimed in claim 1, wherein, for each microchannel section, the depth of each microchannel is between about 2 µm and about 500 µm.

10. The passive microfluidic device as claimed in claim 9, wherein the depth of each microchannel of a last microchannel section is between about 2 micron and about 20 micron.

11. The passive microfluidic device as claimed in claim 1, further comprising:
a respective well connected between the respective microchannels of two sequential microchannel sections of the plurality of microchannel sections.

12. The passive microfluidic device as claimed in claim 1, wherein the passive microfluidic device comprises two microchannel sections, the two microchannel sections comprising a first microchannel section and a last microchannel section.

13. The passive microfluidic device as claimed in claim 12, further comprising:
a well formed between the first microchannel section and the last microchannel section, wherein an outlet of the microchannel of the first microchannel section is connected to the well, and
wherein an inlet of the microchannel of the last microchannel section is connected to the well.

14. The passive microfluidic device as claimed in claim 1, wherein the passive microfluidic device comprises three microchannel sections, the three microchannel sections comprising a first microchannel section, a last microchannel section and an intermediate microchannel section arranged in between the first microchannel section and the last microchannel section.

15. The passive microfluidic device as claimed in claim 14, wherein a width of the microchannel of the intermediate microchannel section is between about 20 µm and about 100 µm.

16. The passive microfluidic device as claimed in claim 14, further comprising:
a first well formed between the first microchannel section and the intermediate microchannel section, wherein an outlet of the microchannel of the first microchannel section is connected to the first well, and wherein an inlet of the microchannel of the intermediate microchannel section is connected to the first well.

17. The passive microfluidic device as claimed in claim 14, further comprising:
a second well formed between the intermediate microchannel section and the last microchannel section, wherein an outlet of the microchannel of the intermediate microchannel section is connected to the second well, and
wherein an inlet of the microchannel of the last microchannel section is connected to the second well.

18. The passive microfluidic device as claimed in claim 1, further comprising:
a surfactant coated on an inner surface of at least one of the respective microchannels of the plurality of microchannel sections.

19. A method of forming a passive counter flow free microfluidic device for sorting a sample of flagellated cells by means of the flagellated cells' intrinsic motility difference, the method comprising:
forming an input reservoir configured to receive the sample of flagellated cells;
forming an output reservoir positioned downstream of the input reservoir, the output reservoir configured to collect the flagellated cells that are sorted; and
forming a plurality of microchannel sections arranged sequentially and in fluid communication with each other between the input reservoir and the output reservoir, and the plurality of microchannel sections designed to define a closed microchannel system between the input reservoir and the output reservoir,
wherein each microchannel section comprises at least one microchannel,
wherein an inlet of the microchannel of a first microchannel section of the plurality of microchannel sections is connected to the input reservoir,
wherein an outlet of the microchannel of a last microchannel section of the plurality of microchannel sections is connected to the output reservoir, and
wherein, for each microchannel section, the total volume of the microchannels of one microchannel section of the plurality of microchannel sections, is larger than that of a subsequent microchannel section disposed in the downstream direction, such that the passive microfluidic device is configured to sort the flagellated cells by means of the flagellated cells' intrinsic motility difference when the flagellated cells move through a stationary fluid medium from the input reservoir to the output reservoir.

20. A method for sorting a sample of flagellated cells by means of the flagellated cells' intrinsic motility difference in the passive counter flow free microfluidic device of claim 1, the method comprising:
supplying a fluid medium to an input reservoir of the passive microfluidic device such that the fluid medium flows towards an output reservoir of the passive microfluidic device;
supplying the sample of flagellated cells to the input reservoir when the fluid medium is in a stationary state; and
sorting the flagellated cells by means of the flagellated cells' intrinsic motility difference when the flagellated cells move through the stationary fluid medium from the input reservoir to the output reservoir.

* * * * *